(12) United States Patent
Meng et al.

(10) Patent No.: US 10,072,122 B2
(45) Date of Patent: Sep. 11, 2018

(54) CARBONATE POLYMER CONTAINING A FUNCTIONAL GROUP OF DISULFIDE FIVE-MEMBERED RING IN THE SIDE CHAIN AND APPLICATION THEREOF

(71) Applicant: BrightGene Bio-Medical Technology Co., Ltd, Suzhou, Jiangsu (CN)

(72) Inventors: Fenghua Meng, Suzhou (CN); Yan Zou, Suzhou (CN); Zhiyuan Zhong, Suzhou (CN); Jiandong Yuan, Suzhou (CN)

(73) Assignee: BRIGHTGENE BIO-MEDICAL TECHNOLOGY (SUZHOU) CO., LTD., Suzhou (CN)

( * ) Notice: Subject to any disclaimer, the term of this patent is extended or adjusted under 35 U.S.C. 154(b) by 61 days.

(21) Appl. No.: 15/314,296

(22) PCT Filed: May 27, 2015

(86) PCT No.: PCT/CN2015/080000
§ 371 (c)(1),
(2) Date: Nov. 28, 2016

(87) PCT Pub. No.: WO2015/180656
PCT Pub. Date: Dec. 3, 2015

(65) Prior Publication Data
US 2017/0190834 A1  Jul. 6, 2017

(30) Foreign Application Priority Data
May 28, 2014 (CN) .......................... 2014 1 0231049

(51) Int. Cl.
C08G 64/30 (2006.01)
A61K 47/34 (2017.01)
(Continued)

(52) U.S. Cl.
CPC .............. *C08G 64/30* (2013.01); *A61K 47/34* (2013.01); *C08G 63/64* (2013.01); *C08G 64/025* (2013.01); *C08G 64/18* (2013.01); *C08G 64/183* (2013.01)

(58) Field of Classification Search
CPC ...... C08G 64/30; C08G 64/18; C08G 64/183; C08G 64/025; C08G 63/64; A61K 47/34
See application file for complete search history.

(56) References Cited

U.S. PATENT DOCUMENTS

| 4,501,905 A | 2/1985 | Krimm et al. |
| 4,754,017 A | 6/1988 | Leitz et al. |

(Continued)

FOREIGN PATENT DOCUMENTS

| CN | 101239966 A | 8/2008 |
| CN | 101891732 A | 11/2010 |

(Continued)

OTHER PUBLICATIONS

Sep. 2, 2015 Search Report issued in International Patent Application No. PCT/CN2015/080000.

(Continued)

*Primary Examiner* — Shane Fang
(74) *Attorney, Agent, or Firm* — Oliff PLC

(57) ABSTRACT

Apparatus relates to a carbonate polymer containing a functional group of disulfide five-membered ring in the side chain and application thereof. The polymer can be prepared from cyclic carbonate monomer containing a disulfide five-membered ring functional group through the activity controllable ring-opening polymerization. For polymer, molecular weight is controlled, molecular weight distribution is narrowed and does not require the protection and deprotection procedures. Polymer prepared from the carbonate monomer through the ring-opening polymerization has (Continued)

biodegradability, can be used for controlling drugs release system, and can be used to prepare tumor-targeted nano-drug carrier which is sensitive to reduction and is reversible cross-linking, can support long circulation in the body, in high concentration of cancers cells can rapidly release cross-linking in the cancer cells, to release drugs, to kill cancer cells with high efficiency and specificity. Biodegradable polymer has a good application value in the tissue engineering and bio-chip coating.

8 Claims, 11 Drawing Sheets

(51) Int. Cl.
*C08G 63/64* (2006.01)
*C08G 64/18* (2006.01)
*C08G 64/02* (2006.01)

(56) References Cited

U.S. PATENT DOCUMENTS

2010/0280219 A1 11/2010 Cooley et al.
2014/0058058 A1 2/2014 Song et al.
2017/0174701 A1 6/2017 Meng et al.

FOREIGN PATENT DOCUMENTS

| CN | 102046679 A | 5/2011 |
| CN | 102245214 A | 11/2011 |
| CN | 104004001 A | 8/2014 |
| CN | 104031248 A | 9/2014 |
| DE | 3607625 A1 | 9/1987 |
| EP | 0057360 A2 | 8/1982 |
| EP | 0236862 A2 | 9/1987 |
| ES | 8308869 A1 | 12/1983 |
| JP | S62212428 A | 9/1987 |
| JP | H09194565 A | 7/1997 |
| JP | 2011520018 A | 7/2011 |
| KR | 20100119491 A | 11/2010 |
| WO | 2009137678 A1 | 11/2009 |
| WO | 2010040188 A1 | 4/2010 |
| WO | 2012116250 A1 | 8/2012 |

OTHER PUBLICATIONS

Sep. 2, 2015 Written Opinion issued in International Patent Application No. PCT/CN2015/080000.
Dec. 13, 2017 Extended Search Report issued in European Patent Application No. 15799082.1.

CARBONATE POLYMER CONTAINING A FUNCTIONAL GROUP OF DISULFIDE FIVE-MEMBERED RING IN THE SIDE CHAIN AND APPLICATION THEREOF

TECHNICAL FIELD

The invention relates to a biodegradable polymer material and its application, in particular to a carbonate polymer containing a functional group of disulfide five-membered ring in the side chain and its application, belonging to the field of medical material.

BACKGROUND TECHNIQUE

Biodegradable polymers have very unique properties, such as their generally good biocompatibility, degradationity in the body, degradation products can be absorbed by the body or excreted through the body's normal physiological pathway, and is widely used in various biomedical fields, such as surgical sutures, bone fixation devices, bio-tissue engineering scaffold materials, and drug-controlled release carrier et. al. Among them, synthetic biodegradable polymers are of particular interest due to their low immunogenicity, their properties such as degradation and mechanical properties, and the like, can be easily controlled. Synthetic biodegradable polymers are mainly aliphatic polyester, polycarbonate, polyamino acid, polyphosphate, polyanhydride, poly orthoester and so on. Among them, polycarbonates such as polytrimethylene cyclic carbonate (PTMC), aliphatic polyester such as polyglycolide (PGA), polylactide (PLA), lactide-glycolide copolymer (PLGA), polycaprolactone (PCL) and so on are the most commonly used biodegradable polymers, has got the permission of the US Food and Drug Administration (FDA).

Technical Problem

However, the existing biodegradable polymers such as PTMC, PCL, PLA and PLGA have simple structure, are lack of functional groups used for modification, it is often difficult to provide a stable cycle of drug nano-carrier or a stable surface modification coating.

Degradation products of polycarbonate are mainly carbon dioxide and neutral glycol, do not produce acid degradation products. The functional cyclic carbonate monomer can be copolymerized with many cyclic ester monomers such as GA, LA and ε-CL, and other cyclic carbonate monomers to obtain biodegradable polymers with different properties.

In addition, in the prior art, in the ring-opening polymerization process, the reactive groups in the cyclic carbonate monomer structure are easy to react, and therefore, in the preparation of the functional polymer from the cyclic carbonate monomer, and the deprotection step, it results in a cumbersome preparation process.

Means for Solving the Problem

Technical Solutions

The aim of the invention is to provide a kind of biodegradable polymer containing a functional group of disulfide five-membered ring in the side chain.

In order to achieve the above-mentioned object, a specific technical solution of the present invention is as follows:

A polymer containing a functional group of disulfide five-membered ring in the side chain, the chemical structure of which is one of the following formulas:

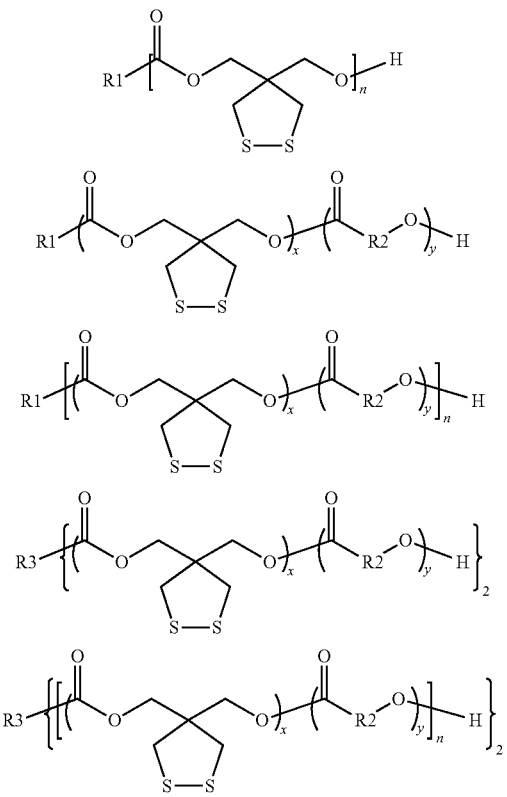

wherein R1 is selected from one of the following groups:

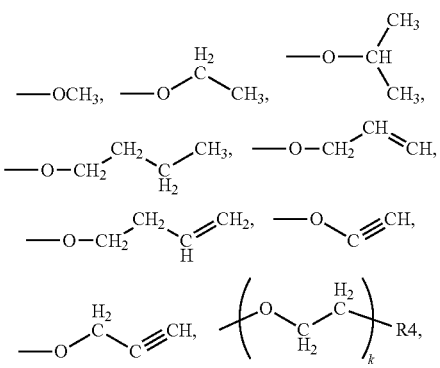

in the formula, k=20-250, R4 is selected from one of the following groups:

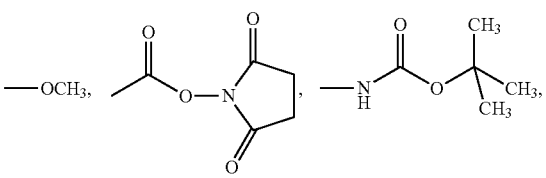

-continued

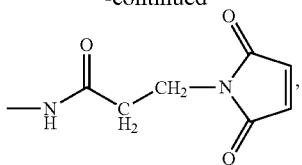

R2 is selected from one of the following groups:

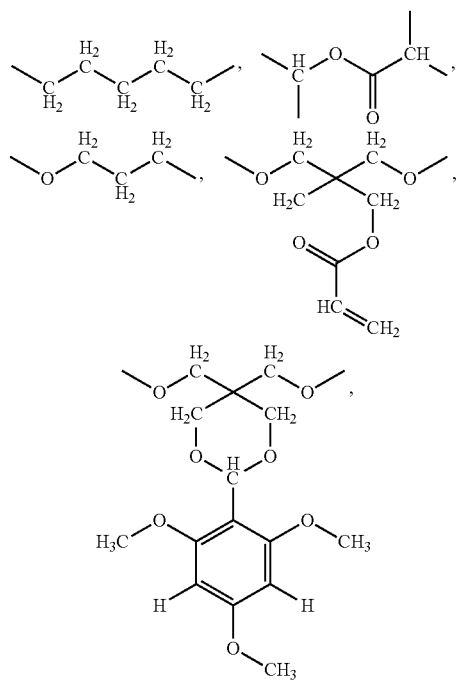

R3 is selected from one of the following groups:

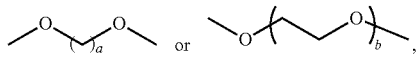

in the formula, a=2, 3 or 4; b=20-250;

the molecular weight of said biodegradable polymer containing a functional group of disulfide five-membered ring in the side chain is 800-100,000 Da.

In the above-mentioned technical scheme, the number of repeating units containing a disulfide five-membered ring functional group in the molecular chain of the biodegradable polymer containing a functional group of disulfide five-membered ring in the side chain is from 4 to 50.

Said biodegradable polymer containing a functional group of disulfide five-membered ring in the side chain can be prepared in the presence of initiator in the solvent, from the cyclic carbonate monomer containing a disulfide five-membered ring functional group through a ring-opening polymerization, or by a ring-opening polymerization among the cyclic carbonate monomer containing a disulfide five-membered ring functional group and other cyclic ester monomer/cyclic carbonate monomer; said other cyclic carbonate monomers include trimethylene cyclic carbonate (TMC), sai other cyclic ester monomers include caprolactone (ε-CL) and lactide (LA) or glycolide (GA).

The chemical structure of the cyclic carbonate monomer containing a disulfide five-membered ring functional group is as follows:

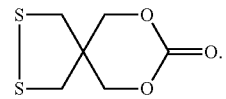 [SMILES: O=C1OCC2(CO1)CSSC2]

It can be prepared by the following steps:

(1) The sodium hydrosulfide monohydrate (NaSH·H$_2$O) was dissolved in N,N-dimethylformamide (DMF) and the dibromo-ne neopentyl glycol was slowly added dropwise with a constant pressure dropping funnel. The reaction was carried out at 50° C. for 48 hours, when the reaction was completed, the reactants was evaporated under reduced pressure to remove the solvent DMF and then diluted with distilled water, extracted four times with ethyl acetate, and finally the organic phase was rotational evaporated to give yellow viscous compound A.

The chemical structure of the compound A is as follows:

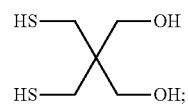

(2) The compound A is preserved in tetrahydrofuran solution, oxidized in the air for 24 hours, to give compound B, chemical structure of the compound B is as follows:

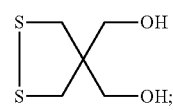

(3) Under nitrogen atmosphere, the compound B and ethyl chloroformate were dissolved in dry tetrahydrofuran. Triethylamine was slowly added dropwise with a constant pressure dropping funnel and reacted in an ice-water bath for 4 hours. When the reaction is completed, the reaction mixture was filtered and the filtrate mixture was concentrated by rotational evaporation and recrystallized from diethyl ether for 3-5 times to give a yellow crystal, that is the cyclic carbonate monomer containing a disulfide five-membered ring functional group.

The above-mentioned cyclic carbonate monomer can be polymerized in the form of polyethylene glycol as the initiator and zinc bis [bis(trimethylsilyl) amide] as the catalyst to form the block polymer. The reaction formula is as follows:

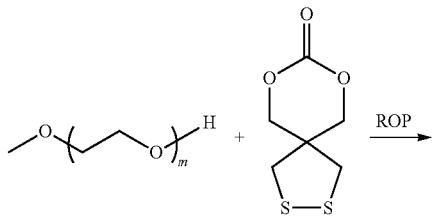

-continued

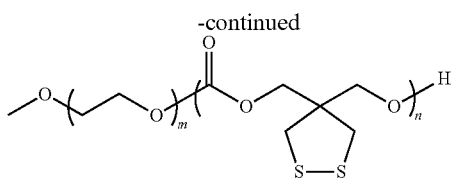

The carbonate polymer containing a functional group of disulfide five-membered ring in the side chain described above has biodegradability, can be prepared into nanoparticles (particle size 20-250 nm), which can be loaded with anticancer drugs; polymer nanoparticles can be catalyzed by reducing agent in catalytic amount such as dithiothreitol or glutathione to form a stable chemistry cross-linking, long circulation in the body; but when enter into the cell in the environment in the presence of a large number of reducing substances, polymer nanoparticles will rapidly release cross-linking, to release drugs, efficiently kill cancer cells. The polymer obtained in the present invention which is prepared for the first time has good biocompatibility, when used as a drug carrier can increase the circulation time of the antitumor drug in the body, increase the enrichment rate of the drug in the tumor site and avoid the damage to the normal tissue of the medicine, can effectively kill tumor cells, with a little effect on normal cells.

The present invention therefore provides a use of the above-described biodegradable polymer containing a functional group of disulfide five-membered ring in the side chain in the preparation of a drug-controlled release carrier; said biodegradable polymer containing a functional group of disulfide five-membered ring in the side chain has a molecular weight of 3,000 to 70,000 Da.

At the same time, the biodegradable polymer containing a functional group of disulfide five-membered ring in the side chain are chemically cross-linked to obtain a cross-linked nano-carrier, and the surface of the cross-linked nano-carrier can be coupled with the tumor cell-specific target molecules such as RGD polypeptides, aptamers, antibodies, folic acid or lactose, etc., can greatly increase the absorption of nano-drugs in cancer cells.

The carbonate polymer containing a functional group of disulfide five-membered ring in the side chain described above has biodegradability, and can be used to prepare biological tissue scaffolds, reducing substances in which the polymers are used in catalytic amounts, for example the environment with the presence of dithiothreitol or glutathione, can promote the polymer after reversible cross-linking to prepare into fibers by electrospinning, such fibers when modified has a good adhesion to cells, through cross-linking can greatly enhance the stability of the fiber, so that it is more stable in the tissue site and avoids the instability and easy-dissociate of the scaffold. The present invention therefore provides a use of the above-described biodegradable polymer containing a functional group of disulfide five-membered ring in the side chain in the preparation of biological tissue engineering scaffold material wherein the molecular weight of the biodegradable polymer containing a functional group of disulfide five-membered ring in the side chain is 5,000 to 100,000 Da.

The present invention also claims the Application of the biodegradable polymer containing a functional group of disulfide five-membered ring in the side chain in the preparation of a biochip coating; the molecular weight of the biodegradable polymer containing a functional group of disulfide five-membered ring in the side chain is 800 to 10,000 Da. The above-mentioned biodegradable polymers containing a functional group of disulfide five-membered ring in the side chain used as a bio-chip coating, similar to the biological tissue scaffold, when catalyzed by a catalytic amount of a reducing agent such as dithiothreitol or glutathione, the polymers can form stable chemical cross-linking, to enhance the bio-chip coating in the body to be more stable, to reduce non-specific adsorption, and to reduce the noise in determination of biological component content.

Effects of the Invention

Beneficial Effects

As a result of the above-mentioned scheme, the invention has the following advantages compared with the prior art:

1. The invention utilizes the cyclic carbonate monomer containing the disulfide five-membered ring functional group for the first time to obtain the biodegradable polymer wherein the molecular weight is controlled, the molecular weight distribution is narrowed by the activity controllable ring-opening homopolymerization or copolymerization with other carbonate monomers and cyclic ester monomers. Since the sulfur-sulfur five-membered ring group does not affect the ring-opening polymerization of the cyclic carbonate monomer, the polymerization process does not require the protection and deprotection procedures in the prior art, simplifies the operation steps.

2. The biodegradable polymer containing a functional group of disulfide five-membered ring in the side chain has excellent biodegradability, can be used for controlling drugs release system, and can be used to prepare tumor-targeted nano-drug carrier which is sensitive to reduction and is reversible cross-linking, can support long circulation in the body, in high concentration of cancers cells can rapidly release cross-linking in the cancer cells, to release drugs, to kill cancer cells with high efficiency and specificity.

3. The cyclic carbonate monomer disclosed in the present invention is easily to be made, and can conveniently take ring-opening polymerization to obtain a biodegradable polymer containing a functional group of disulfide five-membered ring in the side chain; the polymer can be further used for self-assembly in the controlled-drug release systems, tissue engineering and bio-chip coating, has a good application value in the biological materials.

BRIEF DESCRIPTION OF THE DRAWINGS

Description of Drawings

Figure 1:
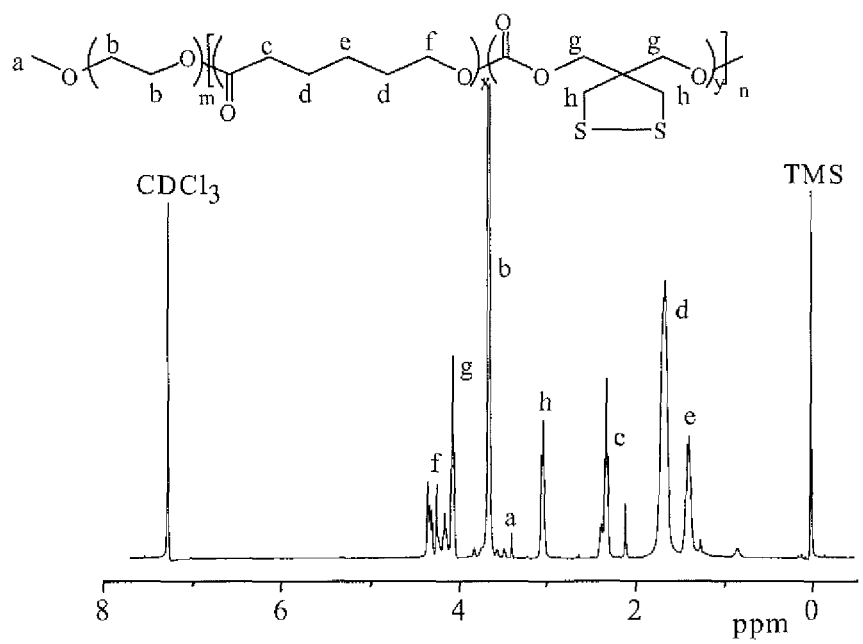
Figure 2:
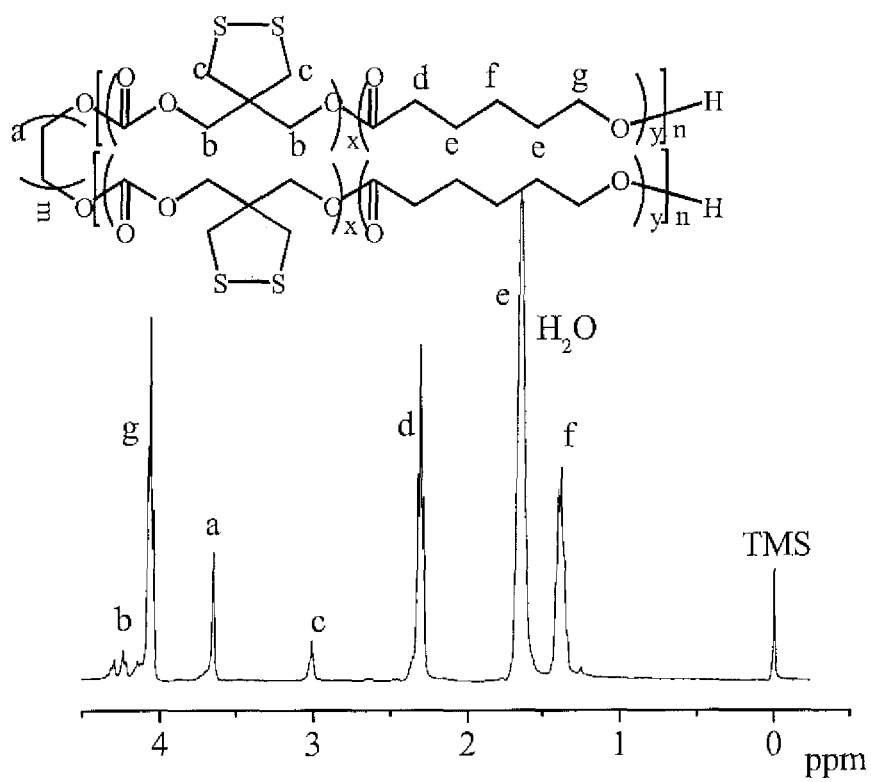
Figure 3:
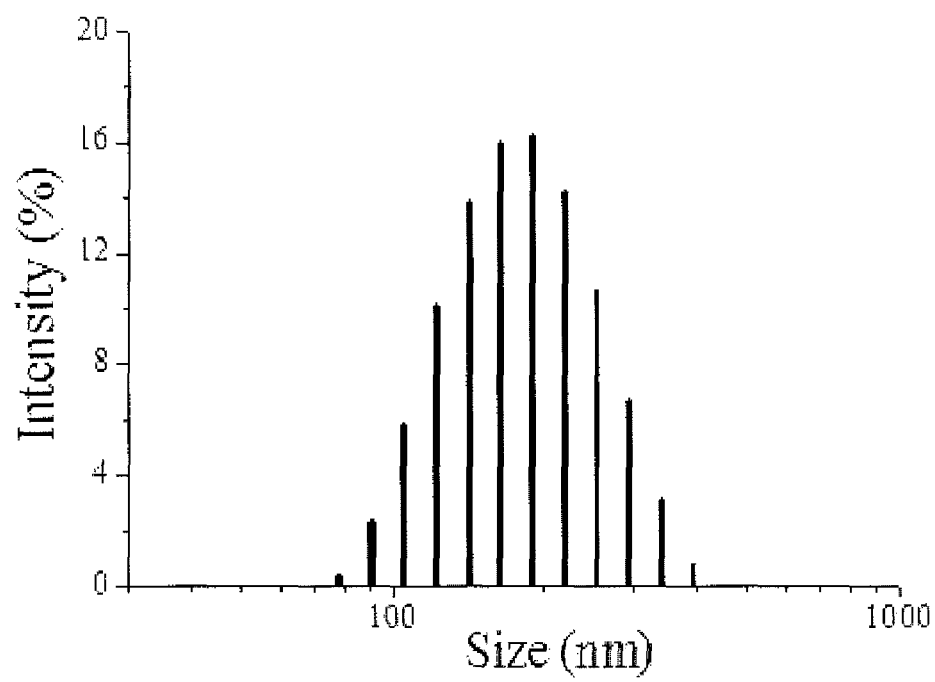
Figure 4:
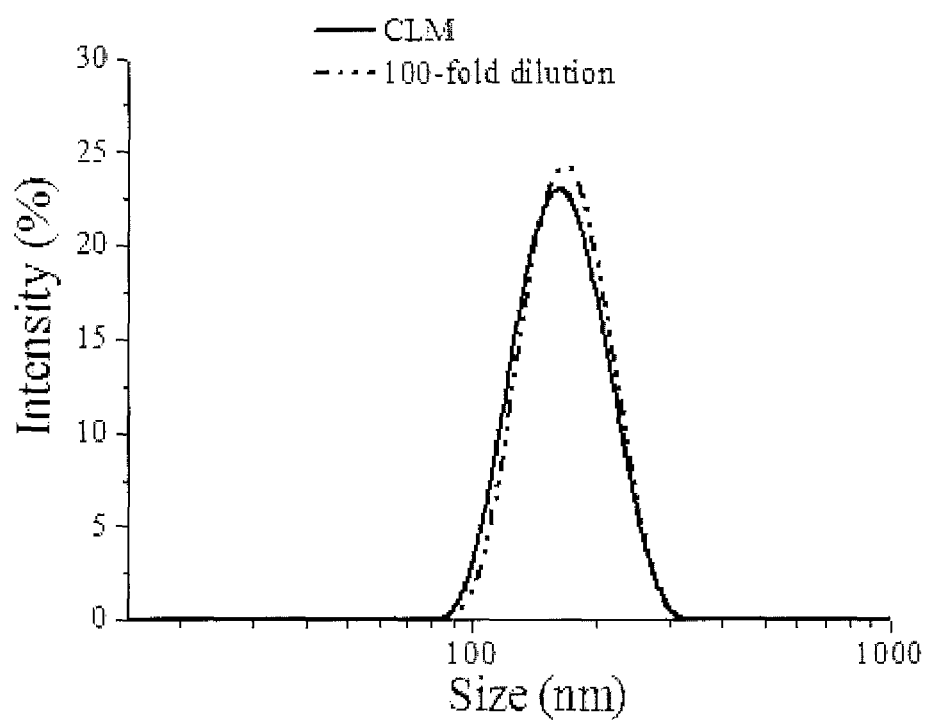
Figure 5:
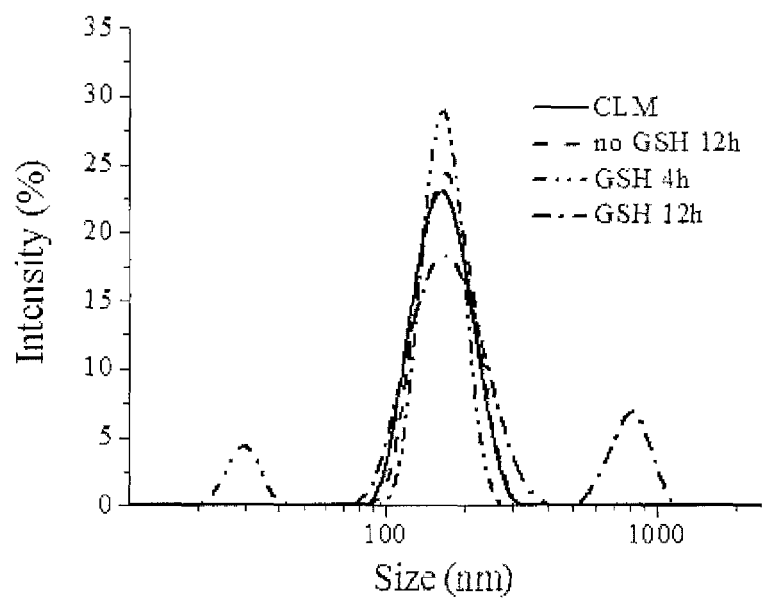
Figure 6:
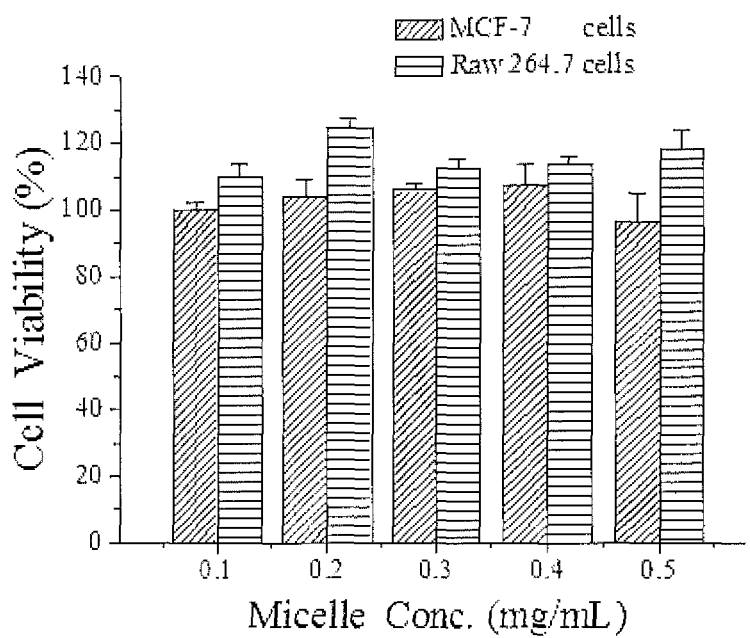
Figure 7:
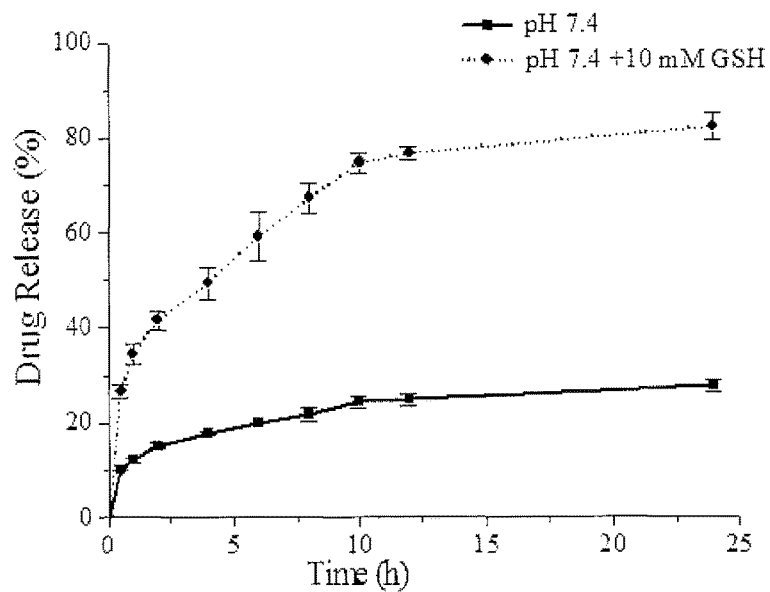
Figure 8:
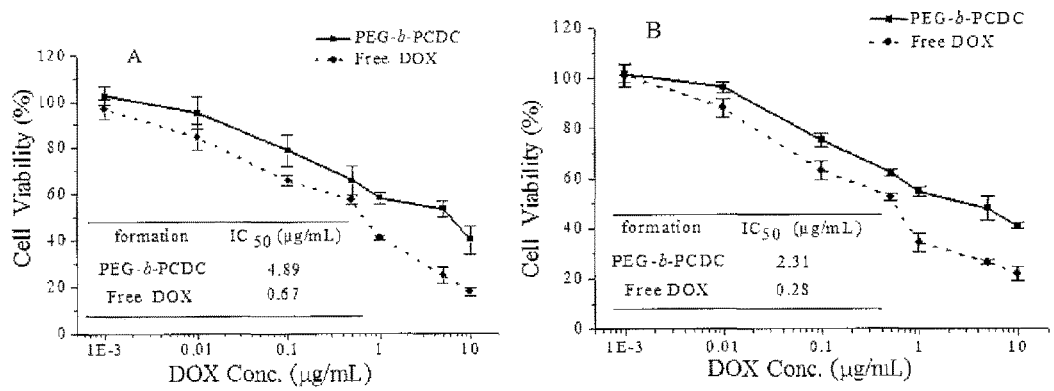
Figure 9:
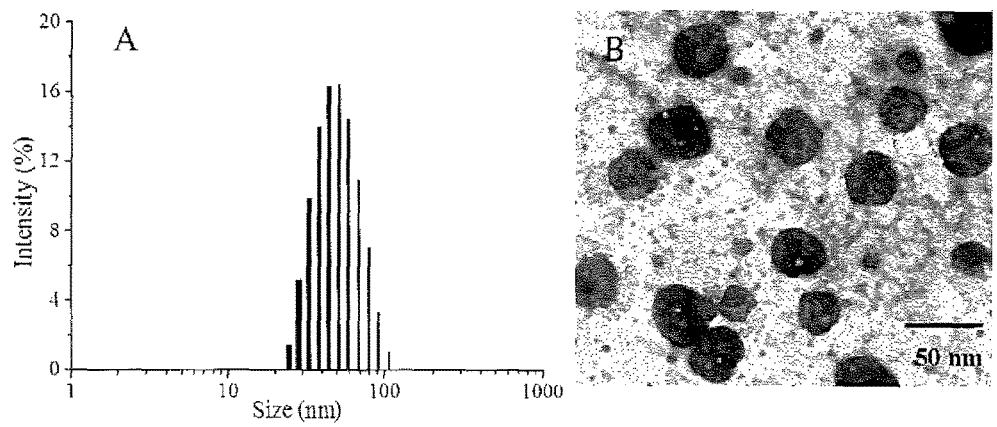
Figure 10:
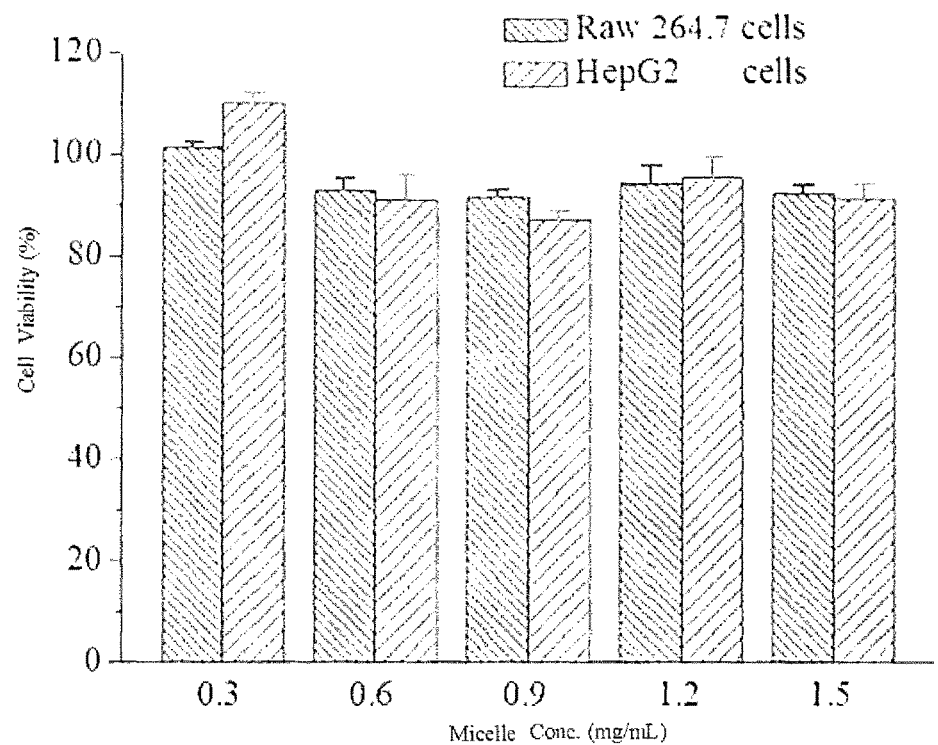
Figure 11:
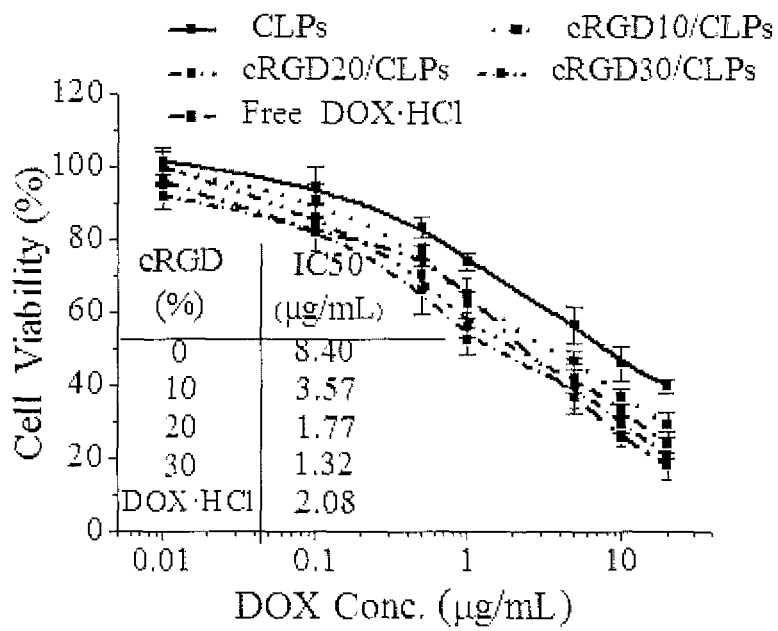
Figure 12:
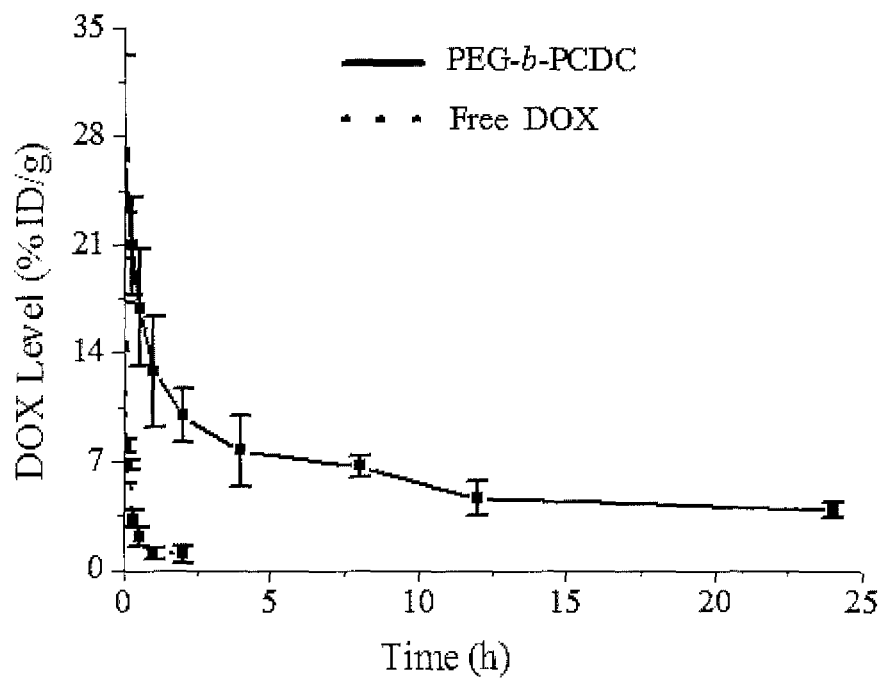
Figure 13:
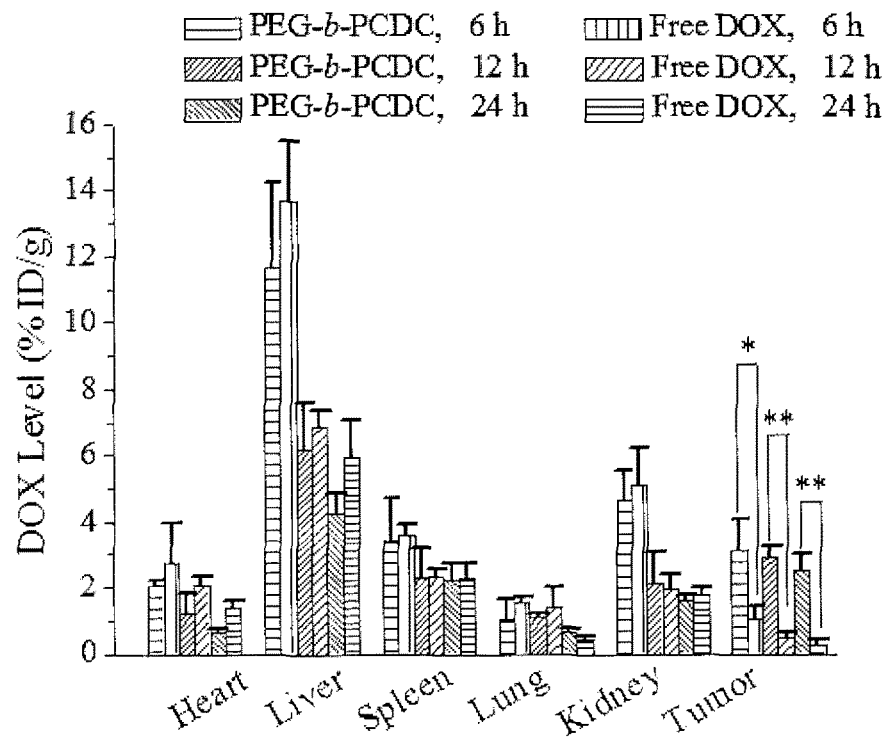
Figure 14:
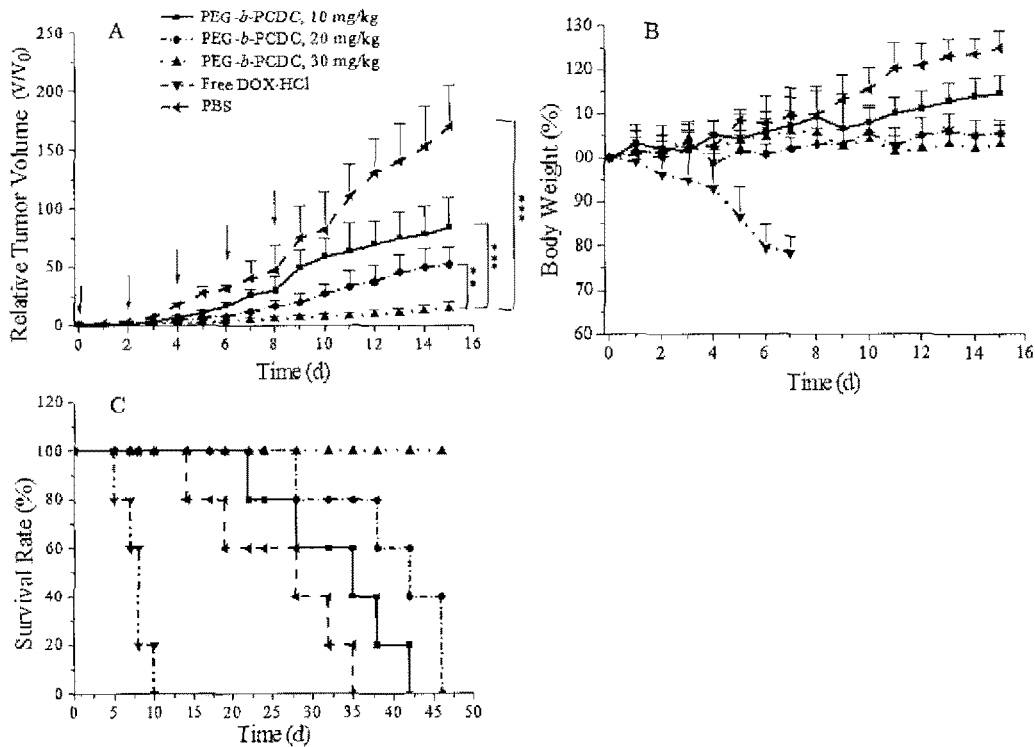
Figure 15:
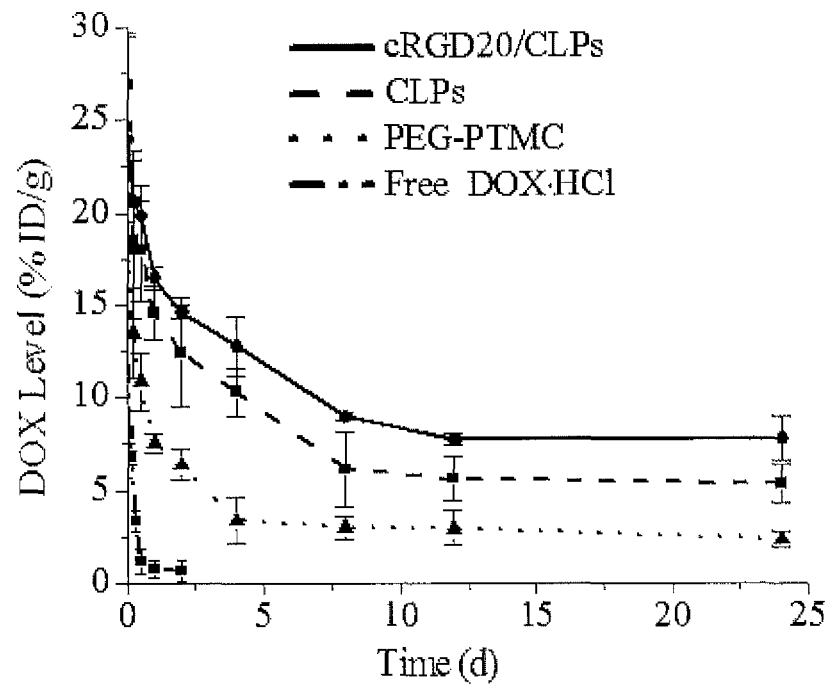
Figure 16:
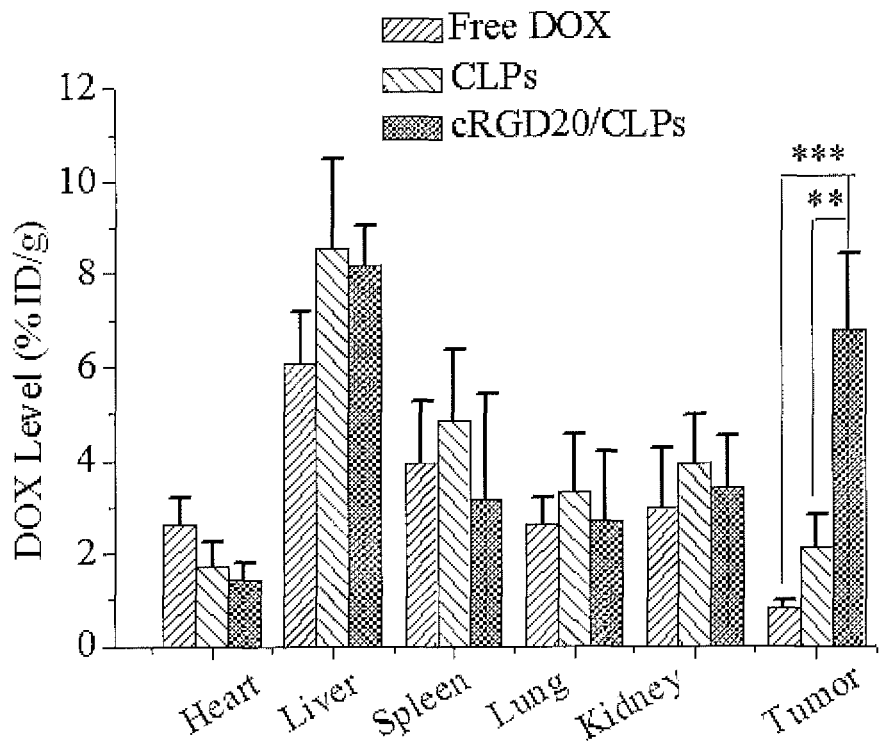
Figure 17:
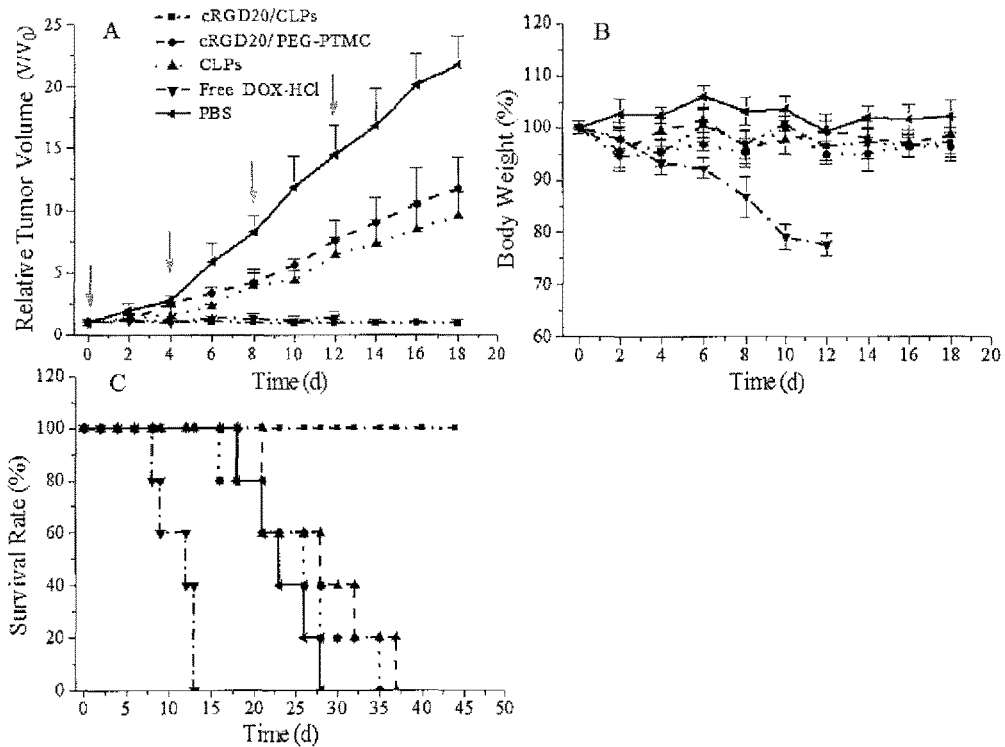
Figure 18:
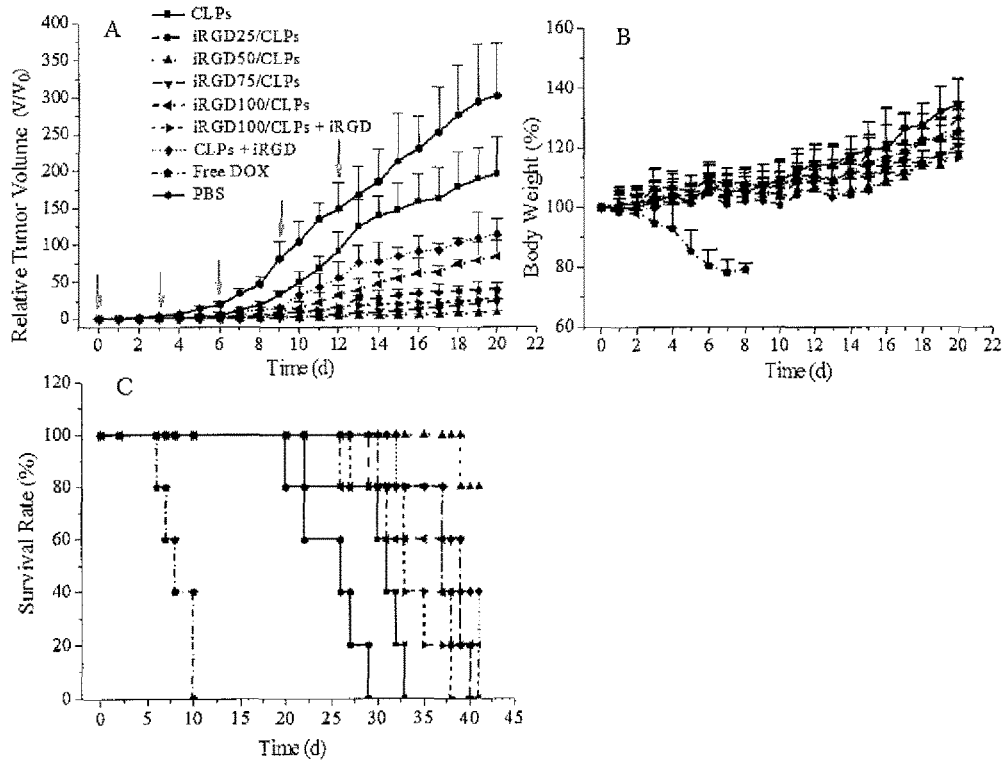
Figure 19:
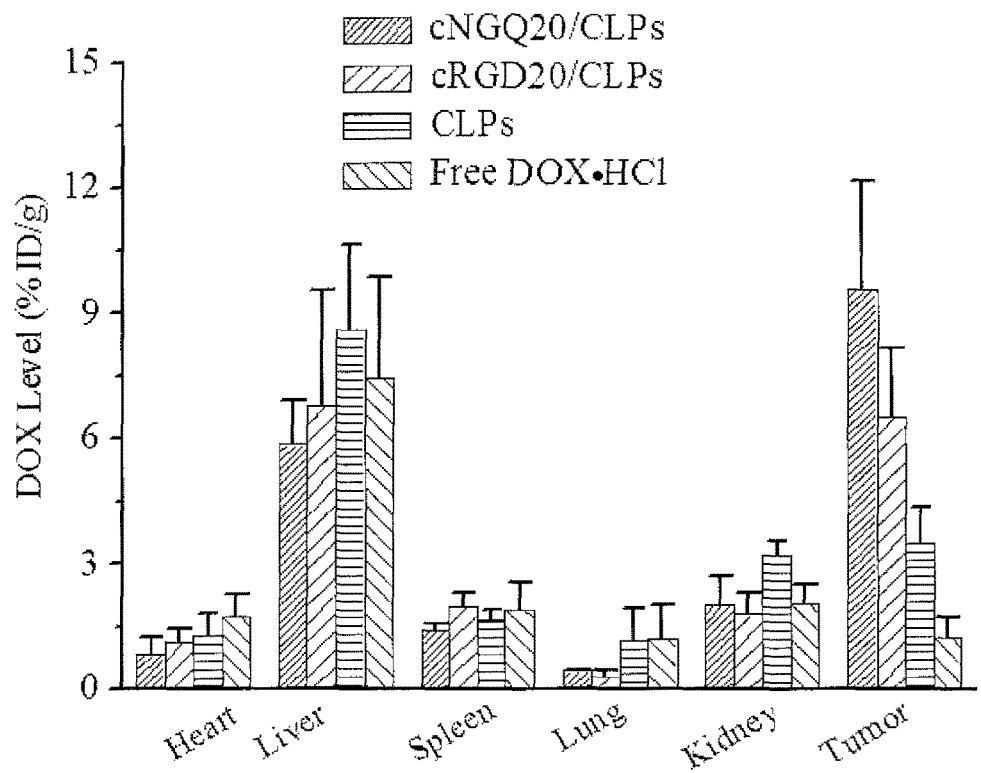
Figure 20:
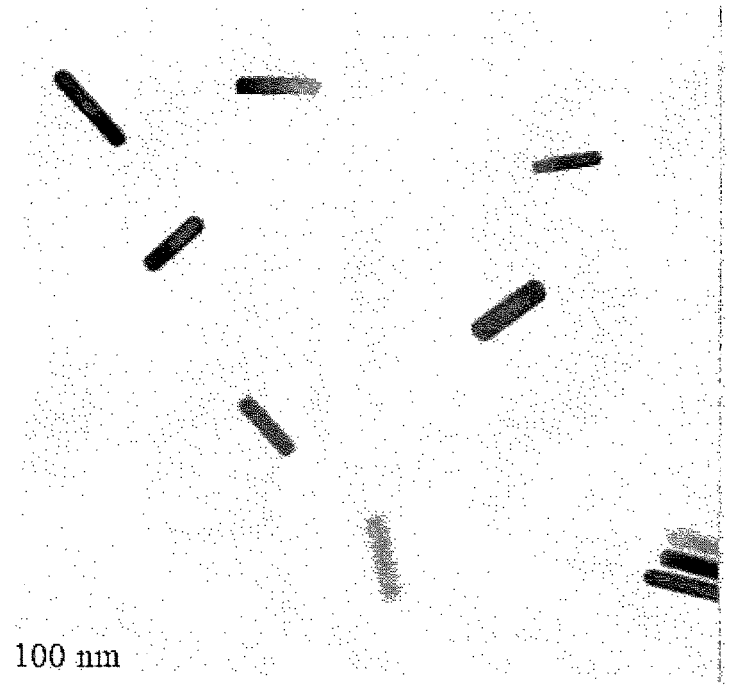
Figure 21:
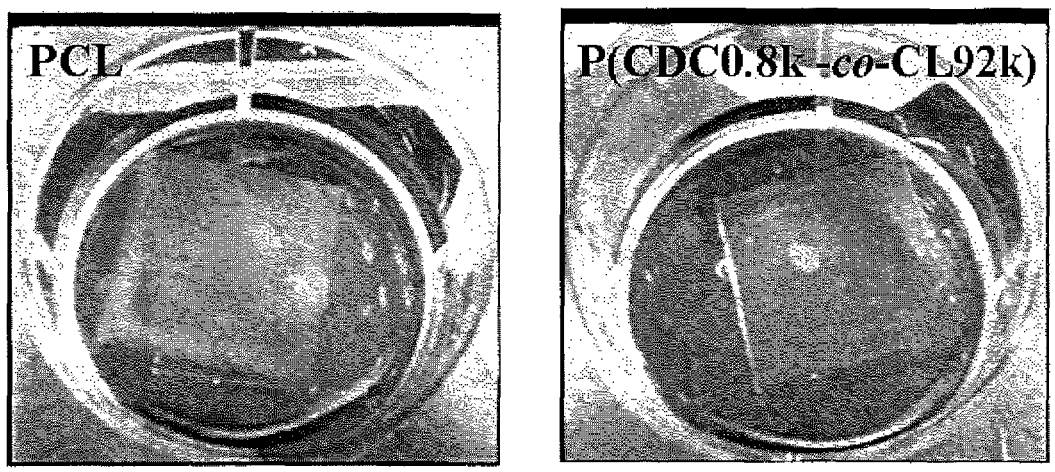

FIG. 1 is a Hydrogen NMR spectrum of the polymer PEG5k-P (CDC2.5k-co-CL3.9k) in Example 2;

FIG. 2 is a NMR spectrum of the polymer P(CDC-co-CL)(6.21k)-PEG(0.5k)-P(CDC-co-CL)(6.21k) in Example 15;

FIG. 3 is a particle size distribution diagram of the polymeric micelle nanoparticles PEG5k-b-PCDC2.8k in Example 16;

FIG. 4 is a graph showing the change in particle diameter of the cross-linked micelle nanoparticle PEG5k-b-PCDC2.8k at high dilution in Example 17;

FIG. 5 is a graph showing the change in particle diameter of the cross-linked micelle nanoparticle PEG5k-b-PCDC2.8k in the presence of the reducing substance glutathione in Example 17;

FIG. 6 is a graph showing the toxicity of cross-linked micelle nanoparticle PEG5k-b-PCDC2.8k to Raw264.7 and MCF-7 cells in Example 17;

FIG. 7 is a graph showing the in vitro release results of the cross-linked micelle nanoparticles PEG5k-b-PCDC2.8k loaded DOX in Example 18;

FIG. 8 is a graph showing the toxicity of the cross-linked micelle nanoparticles PEG5k-b-PCDC2.8k loaded DOX to Raw264.7 and MCF-7 cells in Example 18;

FIG. 9 is a graph showing the particle size distribution and an electron projection microscope of the cross-linked polymer vesicle nanoparticle PEG5k-P (CDC4.9k-co-TMC19k) in Example 19;

FIG. 10 is a graph showing the toxicity of the targeting cross-linked vesicle nanoparticles cRGD-PEG6k-P(CDC4.6k-co-TMC18.6k)/PEG5k-P (CDC4.9k-co-TMC19k) to U87MG cells in Example 19;

FIG. 11 is a graph of toxicity of the targeting cross-linked vesicle nanoparticles loaded DOX to U87MG cells in Example 19;

FIG. 12 is a graph showing the blood circulation in mice of the cross-linked nanoparticle PEG5k-b-PCDC2.8k loaded DOX in Example 20;

FIG. 13 is a graph showing the biodistribution results of the cross-linked nanoparticle PEG5k-b-PCDC2.8k loaded DOX on melanoma bearing mice in Example 21;

FIG. 14 is a graph showing the results of the treatment of the cross-linked nanoparticle PEG5k-b-PCDC2.8k loaded DOX to melanoma bearing mice in Example 22;

FIG. 15 is a blood circulation diagram in a mouse of a targeting cross-linked vesicle loaded DOX in Example 23;

FIG. 16 is the biodistribution profile of targeting cross-linked vesicle loaded DOX to mice bearing human brain malignant glioma in Example 24;

FIG. 17 is a graph showing the therapeutic effect of targeting cross-linked vesicles loaded DOX on mice bearing human brain malignant glioma in Example 25;

FIG. 18 is a graph showing the therapeutic effect of targeting vesicle loaded DOX on melanoma-bearing mice in Example 26;

FIG. 19 is a graph showing the biodistribution of targeting cross-linked vesicles loaded DOX on the lung cancer-bearing mice in Example 27;

FIG. 20 is a TEM image of nano-gold rods modified on the surface of PEG5k-PLGA7.8k-PCDC1.7k in Example 28;

FIG. 21 is a photograph of the polymer PCL and P(CDC0.8k-co-CL92k) when formatted into film and be immersed for two weeks in physiological saline in Example 30.

EXAMPLES FOR THE INVENTION

Detailed Description of the Embodiments

The present invention will further be described in detail below with reference to examples and figs:

Example 1 Synthesis of the Cyclic Carbonate Monomer Containing a Disulfide Five-Membered Ring Functional Group (CDC)

1. The sodium hydrosulfide monohydrate (28.25 g, 381.7 mmol) was dissolved in 400 mL N,N-Dimethylformamide (DMF), then heated at 50° C. until dissolution completely; dibromo-ne neopentyl glycol (20 g, 76.4 mmol) was added dropwise, then reaction was carried out for 48 h. The solvent of DMF was removed by distillation under reduced pressure to the reactants, then was diluted with 200 mL distilled water and extracted four times with 250 mL ethyl acetate, and finally the organic phase was rotary evaporated to give compound A as a yellow viscous, Yield: 70%;

2. The compound A was dissolved in 400 mL tetrahydrofuran solution, oxidized in the air for 24 h, when the sulfydryl between molecules was oxidized to disulfide bond, to give compound B, Yield: >98%;

3. Under nitrogen atmosphere, the compound B (11.7 g, 70.5 mmol) was dissolved in dry tetrahydrofuran (150 mL), stirring until completely dissolved. Then cool to 0° C., and the ethyl chloroformate (15.65 mL, 119.8 mmol) was added, then $Et_3N$ (22.83 mL, 120.0 mmol) was dropwise added. When the addig was completed, the reaction was carried out in an ice-water bath for 4 h. When the reaction is completed, the reaction mixture was filtered to removal the $Et_3N.HCl$ and the filtrate mixture was concentrated by rotational evaporation and recrystallized from diethyl ether for many times to give a yellow crystal, that is the cyclic carbonate monomer containing a disulfide five-membered ring functional group (CDC), Yield: 64%.

Example 2 Synthesis of PEG5k-b-PCDC2.8k Double Block Copolymer Containing a Functional Group of Disulfide Five-Membered Ring in the Side Chain Under a nitrogen atmosphere, 0.3 g (1.56 mmol) CDC monomer, 2 mL dichloromethane were added into a sealing reactor, then 0.5 g (0.1 mmol) polyethylene glycol which molecular weight is 5000 and 1 mL zinc bis[bis(trimethylsilyl)amide] solution (0.1 mol/L) in dichloromethane as the catalyst were added, then the reactor was sealed and moved out of the glovebox, and placed in an oil-bath at 40° C., the reaction was carried out for 1 day, then the reaction was terminated by adding glacial acetic acid, the reaction mixture was precipitated in cold ethyl ether and filtered and dried under vacuum to give product PEG5k-b-PCDC2.8k.

$^1$H NMR (400 MHz, $CDCl_3$): 3.08 (s, —$CCH_2$), 3.30 (m, —$OCH_3$), 4.05 (s, —$CH_2OCOCHCH_2$—), 4.07 (s, —$OCH_2CCH_2O$—), 4.31 (m, —$CCH_2$).

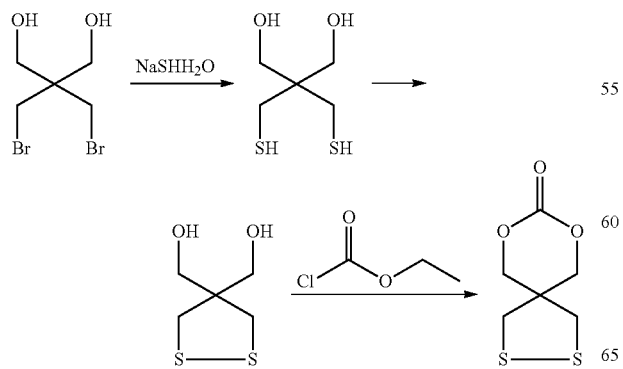

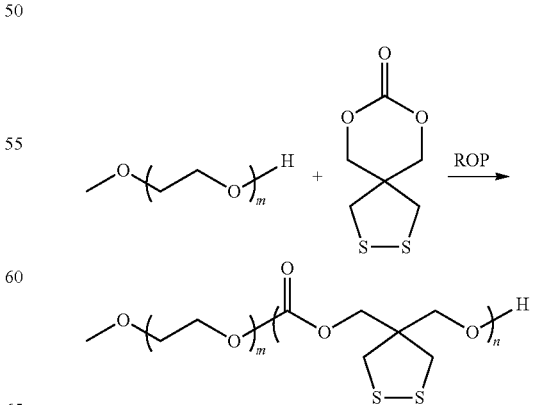

in the formula, m=113.6, n=14.6.

Example 3 Synthesis of PEG5k-P(CDC2.5k-Co-CL3.9k) Double Block Copolymer Containing a Disulfide Five-Membered Ring in the Side Chain Under a nitrogen atmosphere, 0.28 g (1.46 mmol) CDC monomer and 0.4 g (3.51 mmol) caprolactone (ε-CL) were dissolved in 3 mL dichloromethane, then added into a sealing reactor, then 0.5 g (0.1 mmol) polyethylene glycol which molecular weight is 5000 and 0.1 mol/L of zinc bis[bis(trimethylsilyl)amide] solution (0.1 mol/L) in dichloromethane as the catalyst were added, then the reactor was sealed and moved out of the glovebox, and placed in an oil-bath at 40° C., the reaction was carried out for 1 day, then the reaction was terminated by adding glacial acetic acid, the reaction mixture was precipitated in cold ethyl ether and filtered and dried under vacuum to give product PEG5k-P(CDC2.5k-co-CL3.9k). The molecular weight of GPC: 14.0 kDa, molecular weight distribution: 1.56.

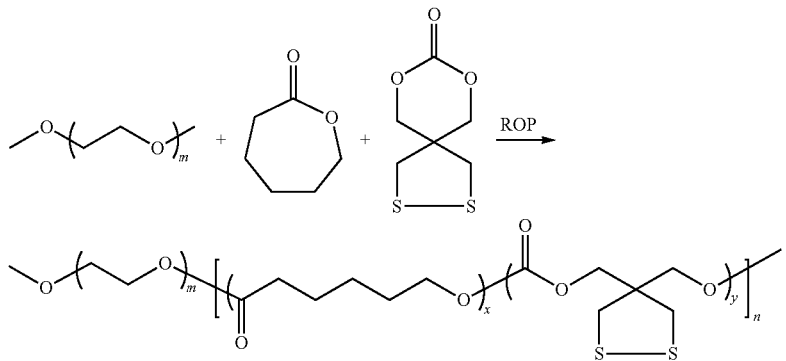

in the formula, m=113.6, x=34.2, y=13.0, n=47.2.

FIG. 1 is a NMR spectrum of the said polymer. $^1$H NMR (400 MHz, CDCl$_3$): 1.40 (m, —COCH$_2$CH$_2$CH$_2$CH$_2$CH$_2$—), 1.65 (m, —COCH$_2$CH$_2$CH$_2$CH$_2$CH$_2$—), 2.30 (t, —COCH$_2$CH$_2$CH$_2$CH$_2$CH$_2$—), 3.08 (s, —CCH$_2$), 3.30 (m, —OCH$_3$), 4.03 (t, —COCH$_2$CH$_2$CH$_2$CH$_2$CH$_2$O—), 4.05 (s, —CH$_2$OCOCHCH$_2$—), 4.07 (s, —OCH$_2$CCH$_2$O—), 4.31 (m, —CCH$_2$).

Example 4 Synthesis of PEG5k-P(CDC3.8k-co-CL14k) Double Block Copolymer Containing a Disulfide Five-Membered Ring in the Side Chain Under a nitrogen atmosphere, 0.5 g (2.6 mmol) CDC monomer and 1.5 g (13.2 mmol) caprolactone (ε-CL) were dissolved in 10 mL dichloromethane, then added into a sealing reactor, then 0.5 g (0.1 mmol) polyethylene glycol which molecular weight is 5000 and 1 mL of zinc bis[bis(trimethylsilyl)amide] solution (0.1 mol/L) in dichloromethane as the catalyst were added, then the reactor was sealed and moved out of the glovebox, and placed in an oil-bath at 40° C., the reaction was carried out for 1 day, then the reaction was terminated by adding glacial acetic acid, the reaction mixture was precipitated in cold ethyl ether and filtered and dried under vacuum to give product PEG5k-P(CDC3.8k-co-CL14k). The molecular weight of GPC: 30.6 kDa, molecular weight distribution: 1.34.

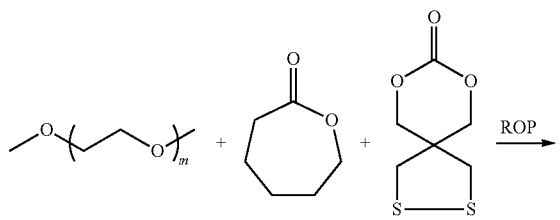

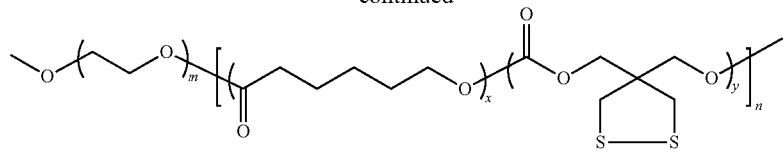

in the formula, m=113.6, x=122.8, y=19.8, n=142.

Example 5 Synthesis of PEG1.9k-P(CDC3.9k-co-CL3.8k) Double Block Copolymer Containing a Disulfide Five-Membered Ring in the Side Chain Under a nitrogen atmosphere, 0.4 g (2.1 mmol) CDC monomer and 0.4 g (3.51 mmol) caprolactone (ε-CL) were dissolved in 3 mL dichloromethane, then added into a sealing reactor, then 0.4 g (0.21 mmol) polyethylene glycol which molecular weight is 1900 and 1 mL of zinc bis[bis(trimethylsilyl)amide] solution (0.1 mol/L) in dichloromethane as the catalyst were added, then the reactor was sealed and moved out of the glovebox, and placed in an oil-bath at 40° C., the reaction was carried out for 1 day, then the reaction was terminated by adding glacial acetic acid, the reaction mixture was precipitated in cold ethyl ether and filtered and dried under vacuum to give product PEG1.9k-P(CDC3.9k-co-CL3.8k). The molecular weight of GPC: 0.96 kDa, molecular weight distribution: 1.35.

Example 7 Synthesis of iPr-P(CDC0.8k-Co-CL92k) Carbonate Polymer Containing a Disulfide Five-Membered Ring in the Side Chain Under a nitrogen atmosphere, 0.1 g (0.52 mmol) CDC monomer and 10 g (87.7 mmol) ε-CL caprolactone (CL) were dissolved in 10 mL dichloromethane, then added into a sealing reactor, then 6 mg (0.1 mmol) isopropyl alcohol and 1 mL of zinc bis[bis(trimethylsilyl)amide] solution (0.1 mol/L) in dichloromethane as the catalyst were added, then the reactor was sealed and moved out of the glovebox, and placed in an oil-bath at 40° C., the reaction was carried out for 2 days, then the reaction was terminated by adding glacial acetic acid, the reaction mixture was precipitated in cold ethyl ether and filtered and dried under vacuum to give product iPr-P(CDC-co-CL)(0.8k-92k). The molecular weight of GPC: 102.3 kDa, molecular weight distribution: 1.36.

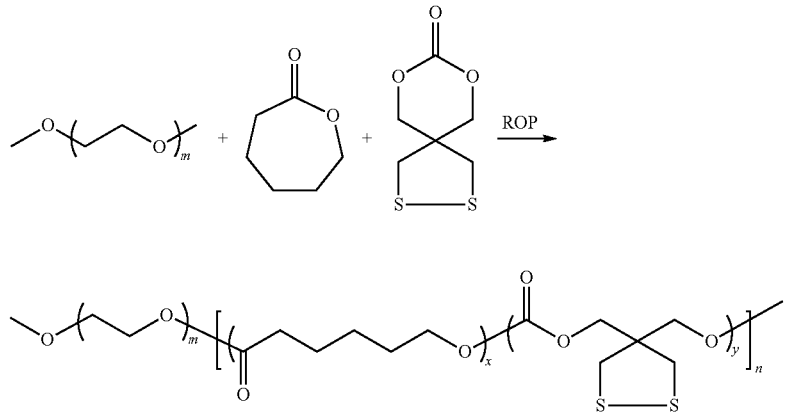

in the formula, m=43.2, x=33.3, y=20.3, n=53.6.

Example 6 Synthesis of Alk-PCDC2.8k Homopolymer Containing a Functional Group of Disulfide Five-Membered Ring in the Side Chain Under a nitrogen atmosphere, 0.3 g (1.6 mmol) CDC monomer was dissolved in 1 mL dichloromethane, then added into a sealing reactor, then 1 mmol/L of refined propargyl alcohol and 1 mL zinc bis[bis(trimethylsilyl)amide] solution (0.1 mol/L) in dichloromethane as the catalyst were added, then the reactor was sealed and moved out of the glovebox, and placed in an oil-bath at 40° C., the reaction was carried out for 1 day, then the reaction was terminated by adding glacial acetic acid, the reaction mixture was precipitated in cold ethyl ether and filtered and dried under vacuum to give product Alk-PCDC2.8k.

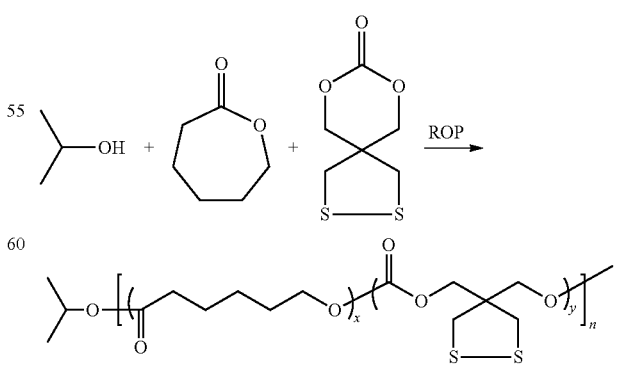

in the formula, x=4.2, y=80.7, n=84.9.

Example 8 Synthesis of PEG5k-PCDC1.0k-PCL3.2k Triple Block Copolymer Containing a Disulfide Five-Membered Ring in the Side Chain Under a nitrogen atmosphere, 0.12 g (1.5 mmol) CDC monomer was dissolved in 2 mL dichloromethane, then added into a sealing reactor, then 0.5 g (0.31 mmol) polyethylene glycol which molecular weight is 5000 and 1 mL of zinc bis[bis(trimethylsilyl)amide] solution (0.1 mol/L) in dichloromethane as the catalyst were added, then the reactor was sealed and moved out of the glovebox, and placed in an oil-bath at 40° C., the reaction was carried out for 1 day, then under a nitrogen atmosphere 0.35 g (0.31 mmol) caprolactone (ε-CL) was added in the glovebox, the reaction was carried out for 1 day, then the reaction was terminated by adding glacial acetic acid, the reaction mixture was precipitated in cold ethyl ether and filtered and dried under vacuum to give product triple block copolymer PEG5k-PCDC1.0k-PCL3.2k. The molecular weight of GPC: 10.4 kDa, molecular weight distribution: 1.45.

$^1$H NMR (400 MHz, CDCl$_3$): 1.40 (m, —COCH$_2$CH$_2$CH$_2$CH$_2$CH$_2$—), 1.65 (m, —COCH$_2$CH$_2$CH$_2$CH$_2$CH$_2$—), 2.30 (t, —COCH$_2$CH$_2$CH$_2$CH$_2$CH$_2$—), 3.08 (s, —CCH$_2$), 3.30 (m, —OCH$_3$), 4.03 (t, —COCH$_2$CH$_2$CH$_2$CH$_2$CH$_2$O—), 4.05 (s, —CH$_2$OCOCHCH$_2$—), 4.07 (s, —OCH$_2$CCH$_2$O—), 4.31 (m, —CCH$_2$).

Example 9 Synthesis of PEG5k-P(CDC3.2k-Co-TMBPEC3.5k) Double Block Copolymer Containing a Disulfide Five-Membered Ring in the Side Chain Under a nitrogen atmosphere, 0.4 g (2.1 mmol) CDC monomer and 0.4 g (1.2 mmol) 2,4,6-trimethoxy benzylidenepentaery thritol carbonate (TMBPEC) were dissolved in 5 mL dichloromethane, then added into a sealing reactor, then 0.5 g (0.1 mmol) polyethylene glycol which molecular weight is 5000 and 1 mL of zinc bis[bis(trimethylsilyl) amide] solution (0.1 mol/L) in dichloromethane as the catalyst were added, then the reactor was sealed and moved out of the glovebox, and placed in an oil-bath at 40° C., the reaction was carried out for 1 day, then the reaction was terminated by adding glacial acetic acid, the reaction mixture was precipitated in cold ethyl ether and filtered and dried under vacuum to give product PEG5k-P(CDC3.2k-co-TMBPEC3.5k). The molecular weight of GPC: 12.4 kDa, molecular weight distribution: 1.47.

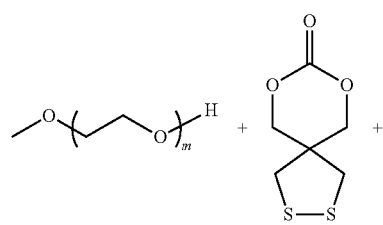

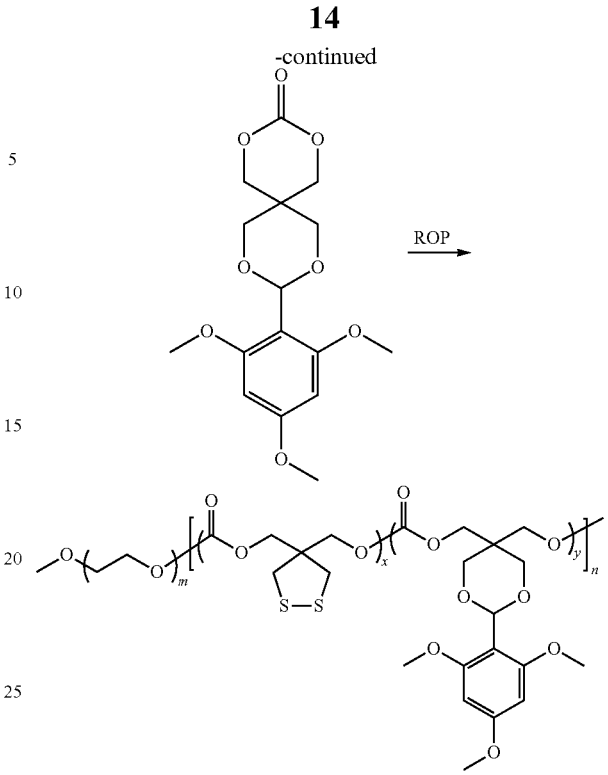

in the formula, m=113.6, x=16.7, y=10.2, n=26.9.

Example 10 Synthesis of PEG1.9k-PCL1.8k-PCDC0.7k Triple Block Copolymer Containing a Functional Group of Disulfide Five-Membered Ring in the Side Chain Under a nitrogen atmosphere, 0.2 g (1.76 mmol) caprolactone (ε-CL) was dissolved in 2 mL dichloromethane, then added into a sealing reactor, then 0.19 g (0.1 mmol) polyethylene glycol which molecular weight is 1900 and 1 mL of zinc bis[bis(trimethylsilyl)amide] solution (0.1 mol/L) in dichloromethane as the catalyst were added, then the reactor was sealed and moved out of the glovebox, and placed in an oil-bath at 40° C., the reaction was carried out for 1 day, then under a nitrogen atmosphere 80 mg (0.42 mmol) CDC monomer was added in the glovebox, the reaction was carried out for 1 day, then the reaction was terminated by adding glacial acetic acid, the reaction mixture was precipitated in cold ethyl ether and filtered and dried under vacuum to give product triple block copolymer PEG1.9k-PCL1.8k-PCDC0.7k. The molecular weight of GPC: 0.64 kDa, molecular weight distribution: 1.32.

$^1$H NMR (400 MHz, CDCl$_3$): 1.40 (m, —COCH$_2$CH$_2$CH$_2$CH$_2$CH$_2$—), 1.65 (m, —COCH$_2$CH$_2$CH$_2$CH$_2$CH$_2$—), 2.30 (t, —COCH$_2$CH$_2$CH$_2$CH$_2$CH$_2$—), 3.08 (s, —CCH$_2$), 3.30 (m, —OCH$_3$), 4.03 (t, —COCH$_2$CH$_2$CH$_2$CH$_2$CH$_2$O—), 4.05 (s, —CH$_2$OCOCHCH$_2$—), 4.07 (s, —OCH$_2$CCH$_2$O—), 4.31 (m, —CCH$_2$).

Example 11 Synthesis of PEG5k-P(CDC4.9k-Co-TMC19k) Double Block Copolymer Containing a Disulfide Five-Membered Ring in the Side Chain Under a nitrogen atmosphere, 0.1 g (0.52 mmol) CDC monomer and 0.4 g (3.85 mmol) trimethylene cyclic carbonate (TMC) were dissolved in 3 mL dichloromethane, then added into a sealing reactor, then 0.1 g (0.02 mmol) polyethylene glycol which molecular weight is 5000 and 0.1 mol/L of zinc bis[bis(trimethylsilyl)amide] solution (0.1 mol/L) in dichloromethane as the catalyst were added, then the reactor was sealed and moved out of the glovebox, and placed in an oil-bath at 40° C., the reaction was carried out for 1 day, then the reaction was terminated by adding glacial acetic acid, the reaction mixture was precipitated in cold ethyl ether and filtered and dried under vacuum to give product PEG5k-P(CDC4.9k-co-TMC19.0k). The molecular weight of GPC: 34.5 kDa, molecular weight distribution: 1.48.

$^1$H NMR (400 MHz, CDCl$_3$): 2.08 (t, —COCH$_2$CH$_2$CH$_2$O—), 3.08 (s, —CCH$_2$), 3.30 (m, —OCH$_3$), 3.65 (t, —OCH$_2$ CH$_2$O—), 4.28 (t, —COCH$_2$CH$_2$CH$_2$O—), 4.31 (m, —CCH$_2$).

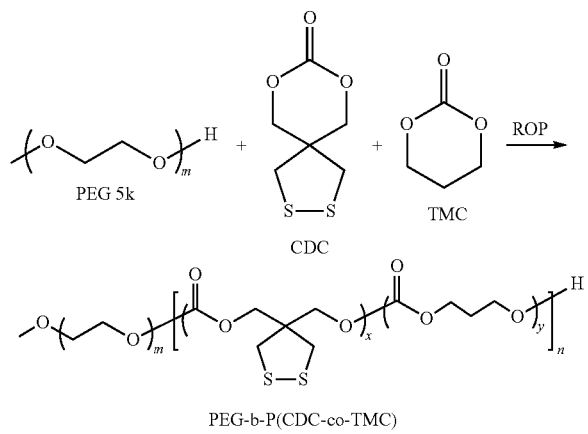

PEG-b-P(CDC-co-TMC)

in the formula, m=113.6, x=25.5, y=186.3, n=211.8.

Example 12 Synthesis of iRGD-PEG6k-P(CDC4.8k-Co-TMC19.2k) Double Block Targeted Copolymer with iRGD Polypeptide Containing a Disulfide Five-Membered Ring in the Side Chain Polymer iRGD-PEG6k-P(CDC4.8k-co-TMC19.2k) was synthesized through two steps, the synthesis of polymer functionalized by maleimide Mal-PEG6k-P(CDC4.8k-co-TMC19.2k) as the first step, which as the same with example 11 except that the mPEG of molecular weight 5000 was replaced by Mal-PEG of molecular weight 6000 Da, which as the initiator for polymerization. $^1$H NMR (400 MHz, CDCl$_3$): 2.08 (t, —COCH$_2$CH$_2$CH$_2$O—), 3.08 (s, —CCH$_2$), 3.30 (m, —OCH$_3$), 3.65 (t, —OCH$_2$ CH$_2$O—), 4.28 (t, —COCH$_2$CH$_2$CH$_2$O—), 4.31 (m, —CCH$_2$), 6.70 (s, Mal). The molecular weight of GPC: 38.6 kDa, molecular weight distribution: 1.42.

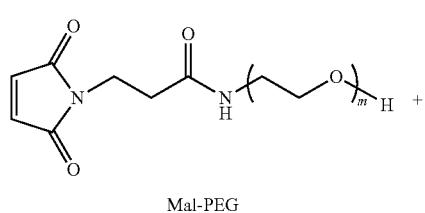

Mal-PEG

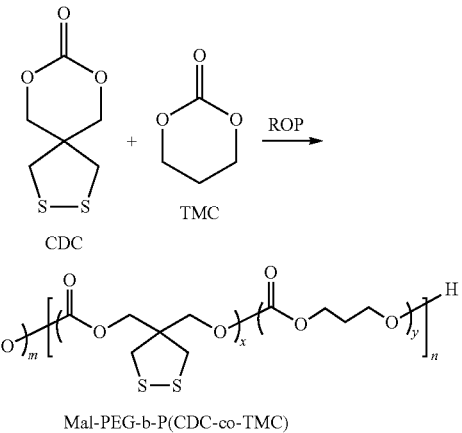

Mal-PEG-b-P(CDC-co-TMC)

in the formula, m=136.4, x=24.8, y=188.4, n=213.2.

The michael addition reaction between iRGD polypeptide and the polymer as got above as the second step. Polymer Mal-PEG6k-P(CDC4.8k-co-TMC19.2k) was dissolved in DMF, then became the nanoparticles with the dropwise adding of PB buffer solution, then the organic solvent was removed by dialysis, then two times the molar weight of iRGD was added, the reaction was carried out at 30° C. for 2 days, then the free iRGD which was not bonded was removed by dialysis, freeze-dried to give the final product iRGD-PEG6k-P(CDC4.8k-co-TMC19.2k). The grafting ratio of iRGD was 92%, by the analysis of nuclear magnetic and BCA protein kit.

Example 13 Synthesis of cRGD-PEG6k-P(CDC4.6k-Co-TMC18.6k) Double Block Targeted Copolymer with cRGD Polypeptide Containing a Disulfide Five-Membered Ring in the Side Chain There were two steps for the synthesis of polymer cRGD-PEG6k-P(CDC4.6k-co-TMC18.6k), which was similar as the example 12, the synthesis of polymer functionalized by N-hydroxysuccinimide NHS-PEG6k-P(CDC4.6k-co-TMC18.6k) as the first step, which as the same with example 11 except that the mPEG which molecular weight is 5000 Da was replaced by NHS-PEG which molecular weight is 6000 Da, which as the initiator for polymerization. $^1$H NMR (400 MHz, CDCl$_3$): 2.08 (t, —COCH$_2$CH$_2$CH$_2$O—), 3.08 (s, —CCH$_2$), 3.30 (m, —OCH$_3$), 3.65 (t, —OCH$_2$ CH$_2$O—), 4.28 (t, —COCH$_2$CH$_2$CH$_2$O—), 4.31 (m, —CCH$_2$), 2.3 (s, NHS). The molecular weight of GPC: 37.6 kDa, molecular weight distribution: 1.38.

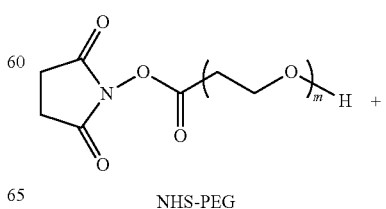

NHS-PEG

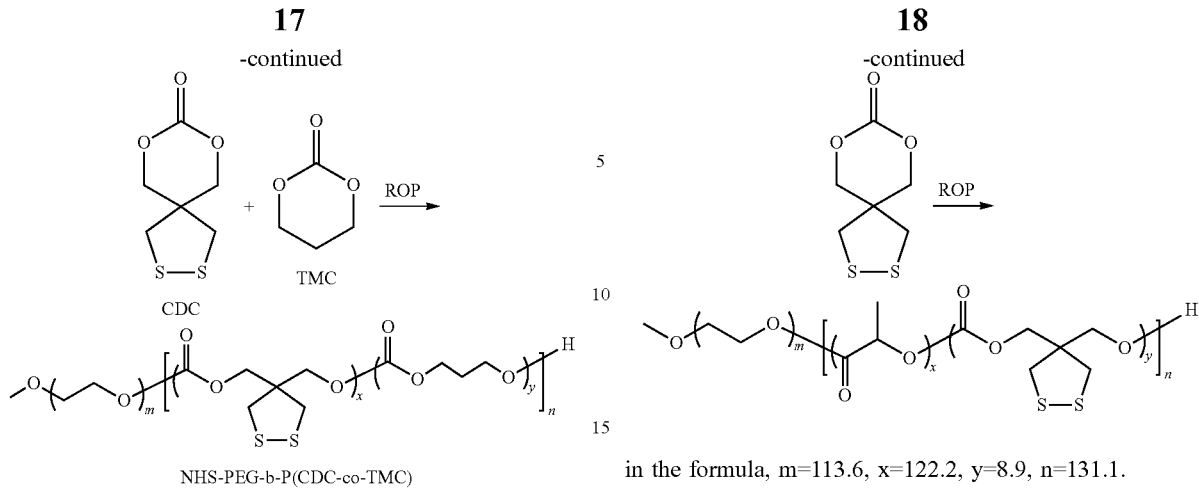

NHS-PEG-b-P(CDC-co-TMC)

in the formula, m=136.4, x=24.0, y=178.8, n=202.8.

The amide reaction for bonding cRGD polypeptide and the polymer as got above as the second step. Polymer said above was dissolved in DMF, then two times the molar weight of cRGD was added, the reaction was carried out at 30° C. for 2 days, then the free cRGD which was not bonded was removed by dialysis, freeze-dried to give the final product cRGD-PEG6k-P(CDC4.6k-co-TMC18.6k). The grafting ratio of cRGD was 88%, by the analysis of nuclear magnetic and BCA protein kit.

Example 14 Synthesis of PEG5k-PLA7.8k-PCDC1.7k Triple Block Copolymer Containing a Disulfide Five-Membered Ring in the Side Chain Under a nitrogen atmosphere, 0.45 g (3.13 mmol) lactide (LA) was dissolved in 3 mL dichloromethane, then added into a sealing reactor, then 0.25 g (0.05 mmol) polyethylene glycol which molecular weight is 5000 and 1 mL of zinc bis[bis(trimethylsilyl)amide] solution (0.1 mol/L) in dichloromethane as the catalyst were added, then the reactor was sealed and moved out of the glovebox, and placed in an oil-bath at 40° C., the reaction was carried out for 1 day, then under a nitrogen atmosphere 100 mg (0.52 mmol) CDC monomer was added in the glovebox, the reaction was carried out for 1 day, then the reaction was terminated by adding glacial acetic acid, the reaction mixture was precipitated in cold ethyl ether and filtered and dried under vacuum to give product triple block copolymer PEG5k-PLA7.8k-PCDC1.7k. The molecular weight of GPC: 16.8 kDa, molecular weight distribution: 1.47.

$^1$H NMR (400 MHz, CDCl$_3$): 1.59 (m, —COCH (CH$_3$) O—), 3.08 (s, —CCH$_2$), 3.30 (m, —OCH$_3$), 3.65 (m, —OCH$_2$CH$_2$O—), 4.07 (s, —OCH$_2$CCH$_2$O—), 5.07 (m, —COCH (CH$_3$).

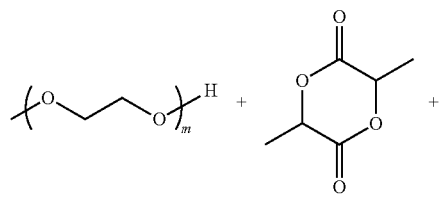

in the formula, m=113.6, x=122.2, y=8.9, n=131.1.

Example 15 Synthesis of P(CDC-Co-CL)(6.21k)-PEG(0.5k)-P(CDC-Co-CL)(6.21k) Triple Block Copolymer Containing a Disulfide Five-Membered Ring in the Side Chain Under a nitrogen atmosphere, 1.5 g (13.2 mmol) ε-CL and 0.0625 g (0.325 mmol) CDC were dissolved in 8 mL dichloromethane, then added into a sealing reactor, then 0.05 g (0.01 mmol) PEG500 and 1 mL of zinc bis[bis(trimethylsilyl)amide] solution (0.1 mol/L) in dichloromethane as the catalyst were added, the reaction was carried out for 1 day, then the reaction was terminated by adding glacial acetic acid, the reaction mixture was precipitated in cold ethyl ether and filtered and dried under vacuum to give product triple block copolymer P(CDC-co-CL)(6.21k)-PEG (0.5k)-P(CDC-co-CL)(6.21k). The molecular weight of GPC: 14.6 kDa, molecular weight distribution: 1.38.

FIG. 2 is a NMR spectrum of the said polymer: $^1$H NMR (400 MHz, CDCl$_3$): 1.40 (m, —COCH$_2$CH$_2$CH$_2$CH$_2$CH$_2$—), 1.65 (m, —COCH$_2$CH$_2$CH$_2$CH$_2$CH$_2$—), 2.30 (t, —COCH$_2$CH$_2$CH$_2$CH$_2$CH$_2$—), 3.08 (s, —CCH$_2$), 4.03 (t, —COCH$_2$CH$_2$CH$_2$CH$_2$CH$_2$O—), 4.05 (s, —CH$_2$OCOCHCH$_2$—), 4.07 (s, —OCH$_2$CCH$_2$O—), 4.31 (m, —CCH$_2$).

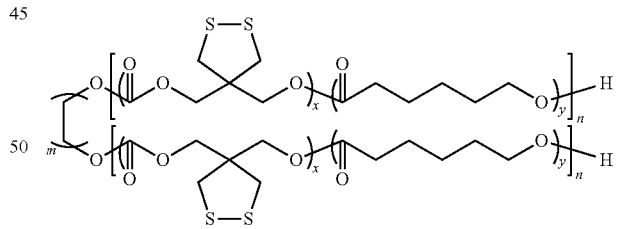

in the formula, m=11.4, x=6.3, y=43.9, n=51.2.

It was known from the above results that, ring-opening homopolymerization or copolymerization of CDC was controllable and the correct molecular weights with the expected and the molecular weight distribution of polymer was narrowed, by the characterization of the polymers.

Example 16 Preparation of the Polymeric Micelle Nanoparticles PEG5k-b-PCDC2.8k Dialysis was used for the preparation of the polymeric micelle nanoparticles. 200 μL of DMF solution of PEG5k-b-PCDC2.8k (2 mg/mL) was dropwise added into 800 μL phosphate buffer (10 mM, pH7.4, PB), then the obtained solution was put in the dialysis bag (MWCO 3500 Da) and dialyzed against PB (10 mM, pH7.4) for one night and change water five times. The size of obtained micelles nanoparticles was 173 nm by dynamic light scattering particle size analyzer (DLS), and the particle size distribution was narrow, which was showed in FIG. 3.

Example 17 Cross-Linking, Decross-Linking and Cytotoxicity of the Polymeric Micelle Nanoparticles PEG5k-b-PCDC2.8k To clearing the air, nitrogen was bubbled into water of micelle nanoparticles for 20 mins, and 10 μL secondary water of dithiothreitol (DTT)(0.007 mg, 4.67×10$^{-5}$ mmol, lipoic acid group moles 10%) was added into nanoparticles solution (1 mL, 0.25 mg/mL, 3.21×10$^{-5}$ mmol) which in the a sealing reactor, the reaction was carried out at room temperature for 1 day with stirring. The measured size of particles was 150 nm after dialysis for 1 day, which was 15% smaller than the size of not cross-linking particles. The particle size and particle size distribution was not change almost when the concentration of cross-linking nanoparticles diluted below the CMC; it was stability in physiological environment, thus it can be seen that the stability of nanoparticles was largely improved by disulfide cross-linking, which was showed in FIG. 4.

Disulfide bond was ruptured under the action of reducing agent such as glutathione (GSH) or DTT. Under a nitrogen atmosphere and at 37° C., nitrogen was bubbled into solution of cross-linking nanoparticles for 10 mins, then GSH was added which final concentration was 10 mM in the solution of cross-linking nanoparticles. The change of the decross-linking size of nanoparticles was follow-up by DLS, which was showed in FIG. 5, the destruction of the size of cross-linking nanoparticles was taken gradually over time after 10 mM GSH was added, which shown that disulfide ring in the polymer was ruptured in reducing agent. So the preparative nano-drug was circulation stability and can rapidly release cross-linking to release drugs when enter into the cell, because the highly concentration of GSH in the cytoplasm.

The toxicity of cross-linked nanoparticle was assayed by MTT. Cell as MCF-7 (human breast cancer cell) and Raw 264.7 (mouse macrophages) were used. HeLa or Raw 264.7 cells were plated in a 96-well plate by 1×10$^4$ cells/mL, 100 μL per well. Culture of different concentration of micelle nanoparticles was added as the experiment group and wells containing only cells and wells containing only culture medium were other setted (quadrupled parallel hole) after cells adherence. Take out the 96-well plate after the cells were cultured for 24 h, 10 μL MTT (5.0 mg/mL) was added. The cells were cultured for another 4 h, then 150 μL Crystal Violet from DMSO dissolution was added, and the absorbance (A) at 492 nm was measured using a microplate reader. The cell viability was determined by comparing the absorbance with control wells containing only culture medium.

$$\text{Cell viability (\%)} = \frac{A_T}{A_C} \times 100\%$$

in the formula, $A_T$ was the absorbance of experiment group at 492 nm, $A_C$ was the absorbance of control group at 492 nm. Concentration of polymer was 0.1, 0.2, 0.3, 0.4 or 0.5 mg/mL. FIG. 6 shown the toxicity of nanoparticle, which shown that the cell viability of Raw 264.7 and MCF-7 was higher than 85% when the concentration of micelle nanoparticle from 0.1 to 0.5 mg/mL, that was shown micelle nanoparticle of PEG5k-b-PCDC2.8k has good biocompatibility.

Example 18 Loaded Drug, In Vitro Release and Cytotoxicity of the Cross-Linked Nanoparticle PEG5k-b-PCDC2.8k Doxorubicin (DOX) was used as a drug, and the whole operation was proceed under dark condition. Desalting the hydrochloride of doxorubicin hydrochloride as the first step, which was proceed as: 1.2 mg (0.002 mmol) DOX was dissolved in 225 μL DMSO, then 0.58 mL (m=0.419 mg, 0.004 mmol) triethylamine was added and stirred for 12 h, then absorbed the above procedure. The concentration of DMSO solution of DOX was 5.0 mg/mL. PEG5k-b-PCDC2.8k was dissolved in DMF, which was mixed with the DMSO solution of DOX according to the predetermined quality ratio for the drug and polymer, then quadrupled secondary water was added slowly with stirring, then takeed a dialysis in water.

The cross-linking for nanoparticle loaded drug was the same as the cross-linking method in Example 17. 100 μL the cross-linked micelle nanoparticle loaded drug was freeze-dried and was dissolved in 3.0 mL DMSO, drug loading efficiency was calculated according to the fluorescence spectroscopy and the standard curve of DOX.

Drug loading content (DLC) and drug loading efficiency (DLE) were calculated according to the following formula:

Drug loading content (wt. %)=(weight of loaded drug/weight of polymer)×100% Drug loading efficiency (%)= (weight of loaded drug/weight of drug in feed)×100%

The loading result of PEG5k-b-PCDC2.8k micelle nanoparticle to DOX was in table 1, showed the efficient loading effect.

TABLE 1 drug loading content and drug loading efficiency of cross-linked polymer nanoparticle loaded Doxorubicin

| polymer | feed ratio (wt. %) | DLC (wt. %) | DLE (%) | size (nm) | size distribution |
|---|---|---|---|---|---|
| PEG5k-b-PCDC2.8k | 5 | 4.0 | 83.3 | 150.3 | 0.17 |
|  | 10 | 7.4 | 80.0 | 162.1 | 0.22 |
|  | 15 | 9.1 | 68.2 | 173.2 | 0.19 |

The in vitro release studies of DOX were conducted in a thermostatic shaker (200 rpm) at 37° C., double duplicate sample per group. The cross-linked micelle nanoparticle loaded DOX released in the PB (10 mM, pH 7.4) of 10 mM GSH which mimicked the intracellular reducing environment as the first group; and the cross-linked micelle nanoparticle loaded DOX released in the PB (10 mM, pH 7.4) as the second group. The concentration of micelle nanoparticle loaded drug was 25 mg/L, and 0.5 mL of release media dialysis against 25 mL of dialysis solvent per tube in the dialysis bag (MWCO: 12,000-14,000). At desired time intervals, 5 mL of release media was taken out and replenished with an equal volume of fresh media of 5 mL. The concentration of drug in the solution was determined using fluorometry EDINBURGH FLS920. FIG. 7 shown the in vitro release results of the DOX with time, showed that release was faster with the GSH mimicked the tumor intracellular added than the control group without GSH. The results showed that the cross-linked micelle nanoparticle loaded drug can released the drug effective in the presence of 10 mM GSH.

The toxicity of cross-linked nanoparticle loaded DOX of PEG5k-b-PCDC2.8k to mouse macrophages Raw 264.7 and human breast cancer cell MCF-7 was assayed by MTT, and decross-linked micelle nanoparticle loaded drug and free drug as the control group. Take Raw 264.7 cell as an example, Raw 264.7 cells were plated in a 96-well plate by 1×10$^4$ cells/mL, 100 μL per well. After cells adherence, Fresh culture containing 0.01, 0.1, 1, 5, 10, 50 and 100 μg/mL solution of cross-linked nanoparticle loaded DOX and free DOX were added as experiment group. Take out the 96-well plate after the cells were cultured for 48 h in incubator, 10 μL MTT (5.0 mg/mL) was added. The cells were cultured for another 4 h, then 150 μL crystal violet from DMSO dissolution was added, and the absorbance (A) at 492 nm was measured using a microplate reader. The cell viability was determined by comparing the absorbance with control wells containing only culture medium.

FIG. 8 shown the toxicity of the said cross-linked micelle nanoparticle loaded drug of PEG5k-b-PCDC2.8k to Raw 264.7 and MCF-7, which shown that the cross-linked micelle nanoparticle loaded DOX with a half-maximal inhibitory concentration of 4.89 μg/mL to Raw 264.7 and 2.31 μg/mL to MCF-7. So the cross-linked nanoparticle loaded DOX can release drugs intracellular, to kill cancer cells with high efficiency.

Example 19 Preparation of the Cross-Linked Polymeric Vesicle Nanoparticles PEG5k-P(CDC4.9k-Co-TMC19k) and its Biocompatibility and the Toxicity of the Cross-Linked Vesicle Loaded Drug to MCF-7, U87MG and A549

The same as example 16, the polymer PEG5k-P(CDC4.9k-co-TMC19k) can become nanoparticle and it has the structure of vesicle by TEM and CLSM, which shown in FIG. 9. It was showed in FIG. 9A that the size of vesicle was 100 nm by DLC and the particle size distribution was narrow. It was showed in FIG. 9B that the vesicle has a hollow structure by TEM. The same as example 17, the vesicle can cross-link and decross-link in the reducing environment. The test for the toxicity of the cross-linked vesicle loaded drug to MCF-7 human breast cancer cell, U87MG human glioma cells and A549 lung cancer cells was the same as example 18. The cell viability of MCF-7, U87MG and A549 was from 85% to 110% when the concentration of micelle nanoparticle from 0.3 mg/mL to 1.5 mg/mL after incubation for 24 h, that was shown micelle nanoparticle of PEG5k-b-PCDC2.8k has good biocompatibility, which was showed in FIG. 10. The toxicity of cRGD targeted cross-linked vesicle loaded drug to U87MG human glioma cells was shown in FIG. 11, which shown half-maximal inhibitory concentration from 3.57 μg/mL dropped to 1.32 μg/mL when the proportion of cRGD targeted polymer from 10% up to 30%, which was close to or low than free drug, and reduced 2.3 to 6.4 times to the cross-linked vesicle loaded drug.

DOX.HCl was loaded by pH-gradients method, and hydrophilic DOX was loaded because the different pH among inside and outside for the vesicle. The cross-linked vesicle loaded drug was prepared with the different proportion of drug inventory from 10% to 30%, then the free drug which was not loaded was dislodged by dialysis, and the size of cross-linked vesicle was 105 to 124 nm by DLS, and the particle size distribution which from 0.10 to 0.15 was narrow, and the efficiency of loading hydrophilic DOX was high (63% to 77%).

Example 20 the Blood Circulation in Mice of the Cross-Linked Nanoparticle PEG5k-b-PCDC2.8k Loaded Drug Aged 4 to 6 weeks old, weight 18 to 20 g C57BL/6 mice (Shanghai Institutes for Biological Sciences Laboratory Animal Center) were collected. They were evenly divided into groups after weighting. Mice were intravenously injected with nanoparticle loaded drug and free drug, and DOX was 10 mg/kg. 10 μL of blood was taken at different time points of 0, 0.25, 0.5, 1, 2, 4, 8, 12 and 24 h, and the weight of blood was calculated with the method of balance. The blood samples upon withdrawing were immediately dissolved in 100 μL 1% triton and 500 μL of extraction solution DMF (containing 1M HCl and 20 mM DTT). Taken the supernatant by centrifugation (20000 rpm, 20 min). The DOX level in the supernatant of each time was determined by fluorometry.

FIG. 12 is a graph showing the blood circulation in mice of the cross-linked nanoparticle PEG5k-b-PCDC2.8k loaded DOX, and time on the horizontal and proportion of the DOX in blood of per gram to the injected DOX (ID %/g) on the vertical. The results showed that circulation time of DOX was short and can not detection at 2 h, but there was 4 ID %/g for cross-linked nanoparticle after 24 h. Half-lives of eliminate in mice was 4.67 h for cross-linked nanoparticle and DOX was 0.21 h only. So cross-linked nanoparticle loaded drug was stability in mice and circulation time was longer.

Example 21 Biodistribution of the Cross-Linked Nanoparticle PEG5k-b-PCDC2.8k Loaded Drug to Mice Bearing Melanoma Tumors Aged 4 to 6 weeks old, weight 18 to 20 g C57BL/6 mice (Shanghai Institutes for Biological Sciences Laboratory Animal Center) were collected. They were evenly divided into groups after weighting. B16 melanoma tumor of 1×10$^6$ cells were generated by subcutaneous injection into the hind flank of the mice. Mice were intravenously injected with nanoparticle loaded drug and DOX (DOX was 10 mg/kg) when the tumor volume reached 100-200 mm$^3$ about two weeks. The mice were sacrificed at 6, 12 or 24 h and the tumor and organs of heart, liver, spleen, lung and kidney were collected, wet weighed, then 500 μL 1% triton was added, homogenized and extracted by 900 μL DMF solution (containing 1 mM HCl and 20 mM DTT). Taken the supernatant by centrifugation (20000 rpm, 20 min). The DOX level at each time was determined by fluorescence measurement.

FIG. 13 is a graph showing the biodistribution results of the cross-linked nanoparticle PEG5k-b-PCDC2.8k loaded DOX on melanoma bearing mice, and organs on the horizontal and proportion of the DOX in organs or tumor of per gram to the injected DOX (ID %/g) on the vertical. Accumulation of nanoparticle loaded drug in tumor was 3.12, 2.93, 2.52 ID %/g at 6, 12, 24 h, which increase 3 to 12 times to the accumulation of DOX which was 1.05, 0.52 and 0.29 ID %/g. The results showed that the enrichment rate of the cross-linked nanoparticle loaded drug in the tumor site was high and lasts longer by EPR.

Example 22 Therapeutic Efficacy of the Cross-Linked Nanoparticle PEG5k-b-PCDC2.8k Loaded Drug to Mice Bearing Melanoma Tumors Aged 4 to 6 weeks old, weight 18 to 20 g C57BL/6 mice (Shanghai Institutes for Biological Sciences Laboratory Animal Center) were collected. They were evenly divided into groups after weighting. B16 melanoma tumor of $1\times10^6$ cells were generated by subcutaneous injection into the hind flank of the mice. Mice were intravenously injected with nanoparticle loaded drug and DOX at 0, 2, 4, 6.8 day when the tumor volume reached 30-50 mm$^3$ about one week, where the DOX proportion of nanoparticle loaded drug was 10, 20, 30 mg/kg and the DOX was 10 mg/kg. The tumor size was measured every day using calipers from 0 to 15 day. The tumor size was calculated by V=(L*W*H)/2 (L was length of tumor, W was width of tumor, H was thickness of tumor). Continue to observe the survival of mice until 46 day.

FIG. 14 is a graph showing the results of the treatment of the cross-linked nanoparticle PEG5k-b-PCDC2.8k loaded DOX to melanoma bearing mice, fig.A for tumor growth suppression, fig.B for body weight change of tumor-bearing mice, fig.C for survival rates of tumor-bearing mice. The results of FIG. 14 showed that effectively inhibited tumor growth at 20 mg DOX equiv./kg after treatment of nanoparticle loaded DOX for 16 day while DOX can inhibited tumor growth with the highly side effect to mice. Mice treated with nanoparticle loaded drug had little change in body weight even the DOX proportion of nanoparticle loaded drug was 30 mg/kg, indicating that they cause little side effects, while body weight of mice treated with DOX was reduced 23% at 7 day, indicating that DOX cause many side effects. 100% survival rate was observed in an experimental period of 46 days at 30 mg DOX equiv./kg of nanoparticle, while 0 survival rate was observed of 10 days of DOX, even that 0 survival rate was observed of 35 days of PBS as control group. As a result, the drug-loading nanoparticles can effectively inhibit tumor growth, and cause little side effects, also can prolong a the survival time of tumor-burdened mice.

Example 23 the Blood Circulation of the Targeting Cross-Linked Vesicle Loaded Drug cRGD-PEG6k-P(CDC4.6k-co-TMC18.6k)/PEG5k-P(CDC4.9k-co-TMC19k)

Aged 4 to 6 weeks old, weight 18 to 20 g Balb/C mice (Shanghai Institutes for Biological Sciences Laboratory Animal Center) were collected. They were evenly divided into groups after weighting. The vesicle was formed with different ratio of cRGD-PEG6k-P(CDC4.6k-co-TMC18.6k) and PEG5k-P(CDC4.9k-co-TMC19k). The results from experiment showed that the size of cross-linked vesicle was 100 nm and the particle size distribution was 0.10 when proportion of cRGD was 20% which had the best targeting. Mice were intravenously injected with targeting vesicle loaded drug cRGD20/CLPs, vesicle loaded drug CLPs, targeting decross-linked vesicle cRGD20/PEG-PTMC and DOX.HCl as control (the DOX was 10 mg/kg). 10 µL of blood was taken at different time points of 0, 0.25, 0.5, 1, 2, 4, 8, 12 and 24 h, and the weight of blood was calculated with the method of balance. The blood samples upon withdrawing were immediately dissolved in 100 µL 1% triton and 500 µL of extraction solution DMF (containing 1M HCl and 20 mM DTT). Taken the supernatant by centrifugation (20000 rpm, 20 min). The DOX level in the supernatant of each time was determined by fluorometry.

FIG. 15 is a graph showing the blood circulation in mice of the targeting cross-linked vesicle loaded DOX, and time on the horizontal and proportion of the DOX in blood of per gram to the injected DOX (ID %/g) on the vertical. The results showed that circulation time of DOX.HCl was short and can not detection at 2 h, but there was 8 ID %/g for cross-linked vesicle after 24 h. Half-lives of eliminate in mice was 4.49 h, 4.26 h and 1.45 h for targeting cross-linked vesicle loaded drug, decross-linked vesicle loaded drug and targeting decross-linked vesicle, while DOX.HCl was 0.27 h only. So targeting cross-linked vesicle loaded drug was stability in mice and circulation time was longer.

Example 24 Biodistribution of the Targeting Cross-Linked Vesicle Loaded Drug cRGD-PEG6k-P(CDC4.6k-co-TMC18.6k)/PEG5k-P(CDC4.9k-co-TMC19k) to Mice Bearing Human Glioma Cells Aged 4 to 6 weeks old, weight 18 to 20 g Balb/C mice (Shanghai Institutes for Biological Sciences Laboratory Animal Center) were collected. They were evenly divided into groups after weighting. U87MG human glioma cells of $5\times10^6$ cells were generated by subcutaneous injection into the hind flank of the mice. Mice were intravenously injected with cRGD20/CLPs, CLPs and DOX.HCl (DOX was 10 mg/kg) when the tumor volume reached 100 to 200 mm$^3$ about 3 to 4 weeks. The mice were sacrificed at 4 h and the tumor and organs of heart, liver, spleen, lung and kidney were collected, wet weighed, then 500 µL 1% triton was added, homogenized and extracted by 900 µL DMF solution (containing 1 mM HCl and 20 mM DTT). Taken the supernatant by centrifugation (20000 rpm, 20 min). The DOX level at each time was determined by fluorescence measurement.

FIG. 16 is the biodistribution profile of targeting cross-linked vesicle loaded DOX to mice bearing human brain malignant glioma, and organs on the horizontal and proportion of the DOX in organs or tumor of per gram to the injected DOX (ID %/g) on the vertical. The results showed that accumulation of DOX in tumor was 6.78, 2.15, 0.82 ID %/g at 4 h for cRGD20/CLPs, CLPs and DOX.HCl, and accumulation for cRGD20/CLPs was 3 times to CLPs and 12 times to DOX.HCl. The results showed that the enrichment rate of the targeting cross-linked vesicle loaded drug in the tumor site was high by active targeting.

Example 25 the Application Therapeutic Efficacy of the cRGD-PEG6k-P(CDC4.6k-co-TMC18.6k)/PEG5k-P(CDC4.9k-co-TMC19k) Targeting Cross-Linked Vesicle Loaded Drug to Mice Bearing Human Glioma Cells Aged 4 to 6 weeks old, weight 18 to 20 g Balb/C mice (Shanghai Institutes for Biological Sciences Laboratory Animal Center) were collected. They were evenly divided into groups after weighting. U87MG human glioma cells of $5\times10^6$ cells were generated by subcutaneous injection into the hind flank of the mice. Mice were intravenously injected with cRGD20/CLPs, CLPs, targeting decross-linked nanoparticle vesicle (cRGD20/PEG-PTMC), DOX.HCl and PBSat 0, 4, 8.12 day when the tumor volume reached 30 to 50 mm$^3$ about two weeks, where the DOX proportion was 10 mg/kg. The tumor size was measured every two days using calipers from 0 to 18 day. The tumor size was calculated by V=(L*W*H)/2 (L was length of tumor, W was width of tumor, H was thickness of tumor). Continue to observe the survival of mice until 45 day.

FIG. 17 is a graph showing the therapeutic effect of cRGD-PEG6k-P(CDC4.6k-co-TMC18.6k)/PEG5k-P(CDC4.9k-co-TMC19k) targeting cross-linked vesicles loaded DOX on mice bearing human brain malignant glioma, fig.A for tumor growth suppression, fig.B for body weight change of tumor-bearing mice, fig.C for survival rates of tumor-bearing mice. The results of FIG. 17 showed that effectively inhibited tumor growth after treatment of cRGD20/CLPs for 18 day and tumor growth after treatment of CLPs and cRGD20/PEG-b-PTMC, while DOX.HCl can inhibited tumor growth with the 21% of declining of body weight to mice at 12 day, indicating that DOX.HCl cause much side effects. Mice treated with cRGD20/CLPs, CLPs and cRGD20/PEG-b-PTMC had little change in body weight, indicating that they cause little side effects. 100% survival rate was observed in an experimental period of 45 days of cRGD20/CLPs, while 0 survival rate was observed of 13 days of DOX.HCl, even that 0 survival rate was observed of 28 days of normal saline group. As a result, the targeting cross-linked vesicles loaded drug can effectively inhibit tumor growth, and cause little side effects, also can prolong a the survival time of tumor-burdened mice.

Example 26 Therapeutic Efficacy of iRGD-PEG6k-P(CDC4.8k-co-TMC19.2k)/PEG5k-P(CDC4.9k-co-TMC19k) Targeting Cross-Linked Vesicles Loaded Drug to Mice Bearing Melanoma Tumors The vesicle was formed with different ratio of iRGD-PEG6k-P(CDC4.8k-co-TMC19.2k) and PEG5k-P(CDC4.9k-co-TMC19k). The size of vesicle was 110 nm and the particle size distribution was 0.12 when proportion of iRGD (internalizing RGD) polymer was 0, 25% and 50%. The function of iRGD was targeting tumor cell and mediated penetrate tumor cell and histamine, and a certain amount of free iRGD enhanced the function of nanoparticle to penetrate tumor histamine. A pH-gradient method was used to load DOX.HCl which had an efficiency of 60 to 80%.

Aged 4 to 6 weeks old, weight 18 to 20 g C57BL/6 mice (Shanghai Institutes for Biological Sciences Laboratory Animal Center) were collected. They were evenly divided into groups after weighting. B16 melanoma tumor of 1×10$^6$ cells were generated by subcutaneous injection into the hind flank of the mice. Mice were intravenously injected with polymer cross-linked vesicles loaded drug which containing 0, 25%, 50% or 100% iRGD, DOX.HCl and PBS at 0, 3, 6, 9, 12 day when the tumor volume reached 30 to 50 mm$^3$ about one week, where the DOX.HCl was 10 mg/kg. The tumor size was measured every day using calipers from 0 to 20 day. The tumor size was calculated by V=(L*W*H)/2 (L was length of tumor, W was width of tumor, H was thickness of tumor). Continue to observe the survival of mice until 46 day.

FIG. 18 is a graph showing the results of the treatment of the targeting vesicles iRGD-PEG6k-P(CDC4.8k-co-TMC19.2k)/PEG5k-P(CDC4.9k-co-TMC19k) loaded DOX to melanoma bearing mice, fig.A for tumor growth suppression, fig.B for body weight change of tumor-bearing mice, FIG. 0 for survival rates of tumor-bearing mice. The results of FIG. 18 showed that effectively inhibited tumor growth after treatment of iRGD50/CLPs for 20 day when the proportion of iRGD was 50%, while it would affect the uptake of nanoparticle to tumor histamine. DOX.HCl can inhibit tumor growth with the 20% of declining of body weight to mice at 8 day, indicating that DOX.HCl cause much side effects. Mice treated with cross-linked vesicles loaded drug which containing any iRGD had little change in body weight, indicating that they cause little side effects. 100% survival rate was observed in an experimental period of 43 days of iRGD50/CLPs, while 0 survival rate was observed of 10 days of DOX.HCl because of the side effects, 0 survival rate was observed of 29 days of PBS group. As a result, the targeting cross-linked vesicles loaded drug can effectively inhibit tumor growth, and cause little side effects, also can prolong a the survival time of tumor-burdened mice.

Example 27 the Blood Circulation, Biodistribution and Inhibit Tumor Growth of the cNGQ-PEG6k-P(CDC4.8k-co-TMC19.2k)/PEG5k-P(CDC4.9k-co-TMC19k) Targeting Cross-Linked Vesicle Loaded Drug to Mice Bearing Lung Cancer Cells The synthesis of polymer cNGQ-PEG6k-P(CDC4.8k-co-TMC19.2k) was similar as the example 13, that was the synthesis of NHS-PEG6k-P(CDC4.8k-co-TMC19.2k) as the first step. The amide reaction for bonding cNGQ polypeptide and the polymer as got above as the second step. The grafting ratio of cRGD was 87%, by the analysis of nuclear magnetic and BCA protein kit. The vesicle was formed with different ratio of cNGQ-PEG6k-P(CDC4.8k-co-TMC19.2k)/PEG5k-P(CDC4.9k-co-TMC19k). A pH-gradient method was used to load DOX.HCl which had an efficiency of 60 to 80%. The results from experiment of in vitro experiment for cells showed the best targeting when proportion of cNGQ was 20% in the vesicle. Half-lives of eliminate in mice of the targeting cross-linked vesicle loaded drug (cNGQ20/CLPs) which was prepared from the vesicle with the proportion of cNGQ was 20% was 4.78 h. The lung cancer model was build subcutaneous the mice by injection the cNGQ20/CLPs modification by near-infrared molecular into the hind flank of the mice as the same as example 24. Results of in vivo imaging confirmed that the concentration of cNGQ20/CLPs to cancer was happened quickly and the fluorescence of cNGQ20/CLPs kept strongly in the tumor site after 48 h. Results of biodistribution confirmed that accumulation of cNGQ20/CLPs was 9 ID %/g in tumor site at 8 h which higher than accumulation of cRGD20/CLPs, CLPs and DOX.HCl, even other viscera. FIG. 19 is a graph showing the biodistribution of targeting cross-linked vesicles loaded DOX on the lung cancer-bearing mice.

The A549 lung cancer model and orthotopic A549 lung tumor with bioluminescence model which can observe tumor growth by bioluminescence from the in vivo imaging were acquired by injecting subcutaneous the mice. After injection the drug into the hind flank of the mice at 0, 4, 8 and 12 day, bioluminescence from the in vivo imaging shown the less fluorescence of lung of the mice treated by cNGQ20/CLPs. It confirmed that cNGQ20/CLPs can target to lung cancer and inhibit tumor growth.

Example 28 Nano-Gold Rods Modified on the Surface of PEG5k-PLGA7.8k-PCDC1.7k Loaded DOX and Drug Release by NIR Synthesis of nano-gold rods modified of PEG5k-PLGA7.8k-PCDC1.7k triple block copolymer nanoparticle: the polymer solution of DMSO (2 mL, 5 mg/mL) was added dropwise into dispersion of nano-gold rods (5 mL, 0.1 mg/mL) under vigorous stirring, then stirred 4 h. The free polymer was removed by centrifugation twice and disperse into phosphate buffer. The yield of polymer modified of nano-gold rods was got by TGA and it was 80% charge to the free polymer (the feeding polymer was 100%).

Loading drug of nano-gold rods modified of polymer: DMSO containing 10%, 20% or 30% DOX was added dropwise into the above said nano-gold rods modified of polymer solution, then stirred for 0.5 h and incubated for 12 h. Free micromolecule was removed by dialysis against phosphate buffer of pH7.4 for 12 h. Loading efficiency of DOX was from 70 to 90% by fluorescence, which says nano-gold rods modified of polymer can load drug efficiently. FIG. 20 is a TEM image of nano-gold rods modified on the surface of PEG5k-PLGA7.8k-PCDC1.7k, which shown length of nano-gold rods was 60 nm and distributed evenly.

Drug release of nano-gold rods modified of polymer by NIR: nano-gold rods modified of polymer were dispersed in 10 mL phosphate buffer and irradiated by infrared light of 0.2 W/cm$^2$ and 808 nm for 5 min every hour. 500 μL solution was taken out at given time and centrifugation, then the release of DOX was got by the fluorescence of supernatant. The release for nano-gold rods modified of polymer after irradiating was 92%, which faster than non irradiating group (18% only). So the nano-gold rods modified of polymer can be used for the release by nearfrared.

Example 29 Polymer PEG1.9k-PCDC0.8k was Used for the Surface of Surface Plasmon Resonance (SPR) Sensor The gold surface of the SPR sensor was previously treated with aqua regia, then washed with ethanol and dried, and then added to a THF solution of triblock polymer PEG1.9k-PCDC0.8k (1 mL, 5 mg/mL). After reacting for 24 h under slow shaking, the sensor chip was taken out and washed three times. The surface density of PEG1.9k modified on the sensor gold plate was 20 nmol/cm$^2$ by XPS, ellipsometer and SPR detection. Compared with the traditional chip, the sensor chip modified by polymer can reduce the non-specific adsorption, improve the stability of measurement and so on, and can be widely used in biomedicine and so on.

Example 30 Cross-Linked Polymer P(CDC0.8k-Co-CL92k) as a Biodegradable Scaffold Material The polymer P(CDC0.8k-co-CL92k) was dissolved in chloroform (40 mg/mL) and film formation on a 1×1 cm$^2$ glass plate (scaffold material). The solvent was removed completely in a vacuum oven for 48 h. The disulfide five-membered ring to cross-linking by heating 10 minutes at 40° C. of heat gun, then soaked in saline for two weeks, it was still intact on the glass plate, however, membrane of PCL as the control group has been off, as FIG. 21, a photograph of the polymer PCL and P (CDC0.8k-co-CL92k) when formatted into film and be immersed for two weeks in physiological saline; Accordingly, the carbonate polymer containing a functional group of disulfide five-membered ring in the side chain could enhance the stability of the scaffold material, could be used as a biological scaffold material.

What is claimed is:

1. A carbonate polymer containing a functional group of disulfide five-membered ring in the side chain, which contains a cyclic carbonate monomer unit containing a disulfide five-membered ring functional group, wherein the chemical structure of the said carbonate polymer containing a functional group of disulfide five-membered ring in the side chain is one of the following formulas:

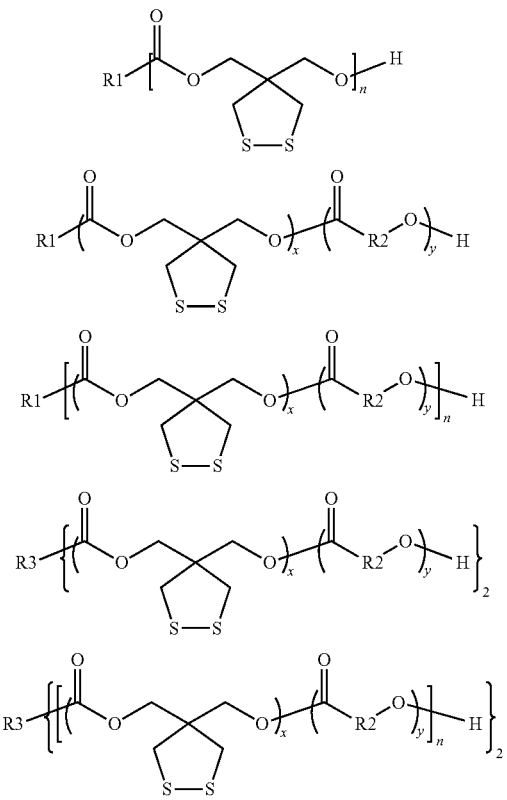

wherein x, y, and n are repeating units,

R1 is selected from one of the following groups:

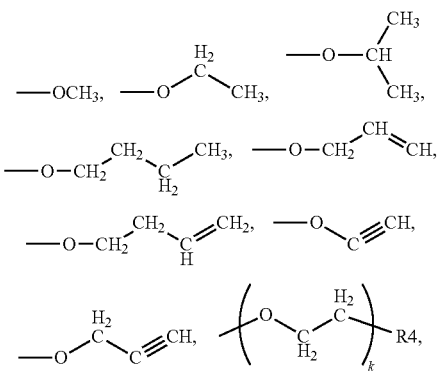

in the formula, k=20-250, R4 is selected from one of the following groups:

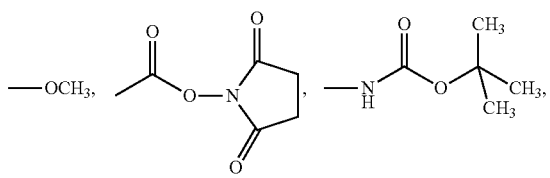

-continued

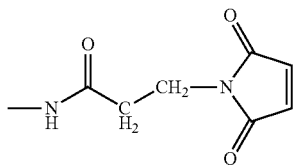

R2 is selected from one of the following groups:

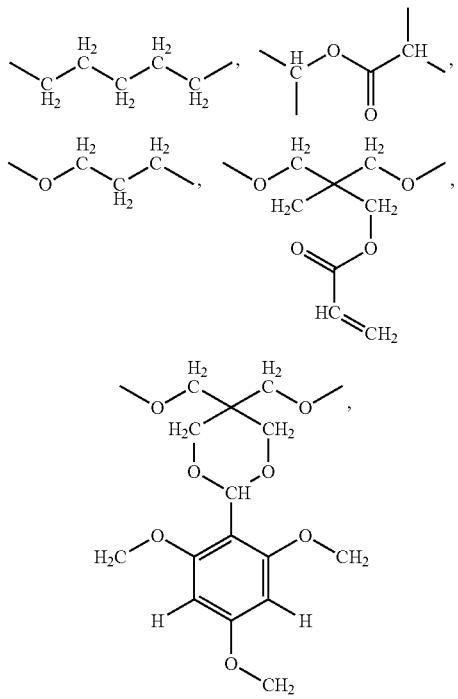

R3 is selected from one of the following groups:

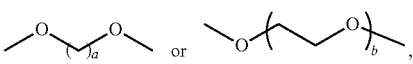

in the formula, a=2, 3 or 4; b=20-250; and
the molecular weight of said carbonate polymer containing a functional group of disulfide five-membered ring in the side chain is 800-100,000 Da.

2. The carbonate polymer containing a functional group of disulfide five-membered ring in the side chain according to claim 1, wherein the number of units of the cyclic carbonate monomer containing a disulfide five-membered ring functional group in the molecular chain of said carbonate polymer containing a functional group of disulfide five-membered ring in the side chain is from 4 to 50.

3. A method for preparing a drug-controlled release carrier, the method comprising utilizing the carbonate polymer of claim 1, the molecular weight of said carbonate polymer being 3,000-70,000 Da.

4. A method for preparing a scaffold material for a biologic tissue engineering, the method comprising utilizing the carbonate polymer of claim 1, the molecular weight of said carbonate polymer being 5,000-100,000 Da.

5. A method for preparing a biochip coating, the method comprising utilizing the carbonate polymer of claim 1, the molecular weight of said carbonate polymer being 800-10,000 Da.

6. A method for preparing a drug-controlled release carrier, the method comprising utilizing the carbonate polymer of claim 2, the molecular weight of said carbonate polymer being 3,000-70,000 Da.

7. A method for preparing a scaffold material for a biologic tissue engineering, the method comprising utilizing the carbonate polymer of claim 2, the molecular weight of said carbonate polymer being 5,000-100,000 Da.

8. A method for preparing a biochip coating, the method comprising utilizing the carbonate polymer of claim 2, the molecular weight of said carbonate polymer being 800-10,000 Da.

* * * * *